(12) United States Patent
Tsuji et al.

(10) Patent No.: US 6,228,592 B1
(45) Date of Patent: May 8, 2001

(54) NUCLEIC ACID DETECTION IN CYTOPLASM

(75) Inventors: Akihiko Tsuji; Masahiko Hirano, both of Shizuoka; Hiroyuki Koshimoto, Kanagawa; Kaname Ishibashi, Shizuoka, all of (JP)

(73) Assignee: Laboratory of Molecular Biophotonics, Shizuoka (JP)

( * ) Notice: Subject to any disclaimer, the term of this patent is extended or adjusted under 35 U.S.C. 154(b) by 0 days.

(21) Appl. No.: 09/476,256

(22) Filed: Dec. 30, 1999

(30) Foreign Application Priority Data

May 12, 1999 (JP) .................................................. 11-131838

(51) Int. Cl.$^7$ .............................. C12Q 1/68; C07H 21/02; C07H 21/04; C12N 15/00
(52) U.S. Cl. ........................... 435/6; 536/23.1; 536/24.3; 935/76; 935/77; 935/78
(58) Field of Search ............................... 435/6; 536/23.1, 536/24.3; 935/76, 77, 78

(56) References Cited

U.S. PATENT DOCUMENTS

| | | |
|---|---|---|
| 4,996,143 | 2/1991 | Heller et al. . |
| 5,225,326 * | 7/1993 | Bresser et al. . |
| 5,728,527 | 3/1998 | Singer et al. . |
| 5,985,549 * | 11/1999 | Singer et al. ............................ 435/6 |

FOREIGN PATENT DOCUMENTS

| | | |
|---|---|---|
| WO93/23570 * | 11/1993 | (WO) . |
| WO98/13524 | 4/1998 | (WO) . |
| WO98/1324 | 8/1998 | (WO) . |

OTHER PUBLICATIONS

Sixou et al., Nucleic Acids Research 22 : 662–668 (1994).*
Zobel et al., Antisense & Nucleic Acid Drug Development 7 :483–493 (1997).*

J. R. Lakowicz, "Principles of Fluorescence Spectroscopy", Plenum Press, New York, pp. 305–309 (1983).

Cardullo et al., "Detection of Nucleic Acid Hybridization by Nonradiative Fluorescence Resonance Energy Transfer", Proc. Natl. Acad. Sci. USA, vol. 85, pp. 8790–8794, Dec. 1988.

Mergny et al., "Fluorescence Energy Transfer as a Probe for Nucleic Acid Structures and Sequences", Nucleic Acids Research, vol. 22, No. 6, pp. 920–928, 1994.

Sixou et al., "Intracellular Oligonucleotide Hybridization Detected by Fluorescence Resonance Energy Transfer (FRET)", Nucleic Acids Research, vol. 22, No. 4, pp. 662–668, 1994.

Leonetti et al., "Intracellular Distribution of Microinjected Antisense Oligonucleotides", Proc. Natl. Acad. Sci. USA, vol. 88, pp. 2702–2706, Apr. 1991.

Fisher et al., "Intracellular Disposition and Metabolism of Fluorescently–Labeled Unmodified and Modified Oligonucleotides Microinjected into Mammalian Cells", Nucleic Acids Research, vol. 21, No. 16, pp. 3857–3865, 1993.

Sokol et al., "Real Time Detection of DNA–RNA Hybridization in Living Cells", Proc. Natl. Acad. Sci. USA, vol. 95, pp. 11538–11543, Sep. 1998.

* cited by examiner

*Primary Examiner*—Ethan Whisenant
(74) *Attorney, Agent, or Firm*—Leydig, Voit & Mayer, Ltd.

(57) ABSTRACT

Detection probes labeled with fluorescent dyes, to which are bound nuclear membrane unpermeable molecules via linkers, having base sequences that can hybridize to a target nucleic acid. The probes are introduced into the cytoplasm of a living cell in which the target nucleic acid is present, and the target nucleic acid is detected by measurement of the change in fluorescence of the fluorescent dyes due to the formation of a hybrid of the target nucleic acid and the probes.

8 Claims, 18 Drawing Sheets

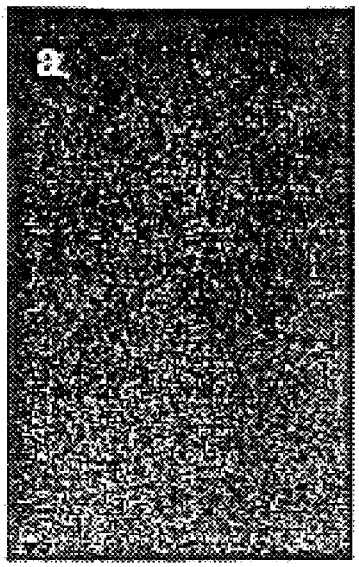 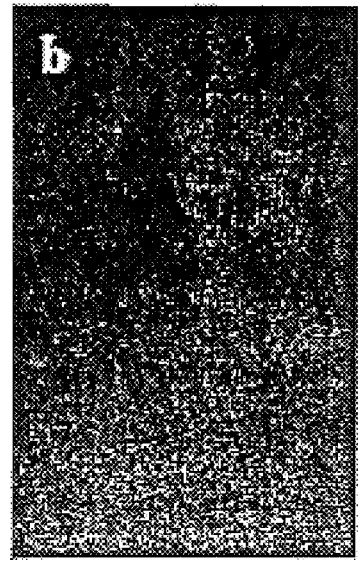 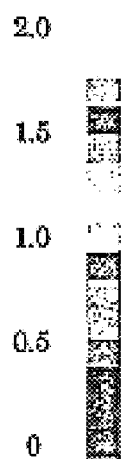
Fig. 16A  Fig. 16B

SEQUENCE LISTING

<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: probe

<400> SEQUENCE: 1
gaacatcatc gtggcggtta                                                       20

<210> SEQ ID NO 2
<211> LENGTH: 20
<212> TYPE: DNA
<213> ORGANISM: Artificial Sequence
<220> FEATURE:
<223> OTHER INFORMATION: probe

<400> SEQUENCE: 2
tagtctgcgt tgaagcccga                                                       20

<210> SEQ ID NO 3
<211> LENGTH: 20
<212> TYPE: DNA
<213> ORGANISM: Artificial Sequence
<220> FEATURE:
<223> OTHER INFORMATION: probe

<400> SEQUENCE: 3
tctagttggt ctgtctccgc                                                       20

<210> SEQ ID NO 4
<211> LENGTH: 20
<212> TYPE: DNA
<213> ORGANISM: Artificial Sequence
<220> FEATURE:
<223> OTHER INFORMATION: probe

<400> SEQUENCE: 4
gcaaagcaga cttctcatct                                                       20

<210> SEQ ID NO 5
<211> LENGTH: 20
<212> TYPE: DNA
<213> ORGANISM: Artificial Sequence
<220> FEATURE:
<223> OTHER INFORMATION: probe

<400> SEQUENCE: 5
tccggggtgg caacctctgg                                                       20

<210> SEQ ID NO 6
<211> LENGTH: 20
<212> TYPE: DNA
<213> ORGANISM: Artificial Sequence
<220> FEATURE:
<223> OTHER INFORMATION: probe

<400> SEQUENCE: 6
gggtgaaggc ctcctcagac                                                       20

<210> SEQ ID NO 7
<211> LENGTH: 20

```
<212> TYPE: DNA
<213> ORGANISM: Artificial Sequence
<220> FEATURE:
<223> OTHER INFORMATION: probe

<400> SEQUENCE: 7
aaggactaag gagaaagaga                                               20

<210> SEQ ID NO 8
<211> LENGTH: 20
<212> TYPE: DNA
<213> ORGANISM: Artificial Sequence
<220> FEATURE:
<223> OTHER INFORMATION: probe

<400> SEQUENCE: 8
agattagtta atgctatgag                                               20

<210> SEQ ID NO 9
<211> LENGTH: 20
<212> TYPE: DNA
<213> ORGANISM: Artificial Sequence
<220> FEATURE:
<223> OTHER INFORMATION: probe

<400> SEQUENCE: 9
gaacatcatc gtggcggtta                                               20

<210> SEQ ID NO 10
<211> LENGTH: 20
<212> TYPE: DNA
<213> ORGANISM: Artificial Sequence
<220> FEATURE:
<223> OTHER INFORMATION: probe

<400> SEQUENCE: 10
tctagttggt ctgtctccgc                                               20

<210> SEQ ID NO 11
<211> LENGTH: 20
<212> TYPE: DNA
<213> ORGANISM: Artificial Sequence
<220> FEATURE:
<223> OTHER INFORMATION: probe

<400> SEQUENCE: 11
tccggggtgg caacctctgg                                               20

<210> SEQ ID NO 12
<211> LENGTH: 20
<212> TYPE: DNA
<213> ORGANISM: Artificial Sequence
<220> FEATURE:
<223> OTHER INFORMATION: probe

<400> SEQUENCE: 12
aaggactaag gagaaagaga                                               20

<210> SEQ ID NO 13
<211> LENGTH: 20
<212> TYPE: DNA
<213> ORGANISM: Artificial Sequence
<220> FEATURE:
<223> OTHER INFORMATION: probe

<400> SEQUENCE: 13
```

```
tagtctgcgt tgaagcccga                                              20

<210> SEQ ID NO 14
<211> LENGTH: 20
<212> TYPE: DNA
<213> ORGANISM: Artificial Sequence
<220> FEATURE:
<223> OTHER INFORMATION: probe

<400> SEQUENCE: 14
gcaaagcaga cttctcatct                                              20

<210> SEQ ID NO 15
<211> LENGTH: 20
<212> TYPE: DNA
<213> ORGANISM: Artificial Sequence
<220> FEATURE:
<223> OTHER INFORMATION: probe

<400> SEQUENCE: 15
gggtgaaggc ctcctcagac                                              20

<210> SEQ ID NO 16
<211> LENGTH: 20
<212> TYPE: DNA
<213> ORGANISM: Artificial Sequence
<220> FEATURE:
<223> OTHER INFORMATION: probe

<400> SEQUENCE: 16
agattagtta atgctatgag                                              20

<210> SEQ ID NO 17
<211> LENGTH: 20
<212> TYPE: DNA
<213> ORGANISM: Artificial Sequence
<220> FEATURE:
<223> OTHER INFORMATION: probe

<400> SEQUENCE: 17
gcggagacag accaactaga                                              20

<210> SEQ ID NO 18
<211> LENGTH: 20
<212> TYPE: DNA
<213> ORGANISM: Artificial Sequence
<220> FEATURE:
<223> OTHER INFORMATION: probe

<400> SEQUENCE: 18
agatgagaag tctgctttgc                                              20

<210> SEQ ID NO 19
<211> LENGTH: 20
<212> TYPE: DNA
<213> ORGANISM: Artificial Sequence
<220> FEATURE:
<223> OTHER INFORMATION: probe

<400> SEQUENCE: 19
tctagttggt ctgtctccgc                                              20

<210> SEQ ID NO 20
<211> LENGTH: 20
<212> TYPE: DNA
<213> ORGANISM: Artificial Sequence
```

```
<220> FEATURE:
<223> OTHER INFORMATION: probe

<400> SEQUENCE: 20
gcaaagcaga cttctcatct                                                    20

<210> SEQ ID NO 21
<211> LENGTH: 20
<212> TYPE: DNA
<213> ORGANISM: Artificial Sequence
<220> FEATURE:
<223> OTHER INFORMATION: probe

<400> SEQUENCE: 21
tctagttggt ctgtctccgc                                                    20

<210> SEQ ID NO 22
<211> LENGTH: 20
<212> TYPE: DNA
<213> ORGANISM: Artificial Sequence
<220> FEATURE:
<223> OTHER INFORMATION: probe

<400> SEQUENCE: 22
gcaaagcaga cttctcatct                                                    20

<210> SEQ ID NO 23
<211> LENGTH: 40
<212> TYPE: RNA
<213> ORGANISM: Artificial Sequence
<220> FEATURE:
<223> OTHER INFORMATION: probe

<400> SEQUENCE: 23
gcggagacag accaacuaga agaugagaag ucugcuuugc                              40

<210> SEQ ID NO 24
<211> LENGTH: 40
<212> TYPE: DNA
<213> ORGANISM: Artificial Sequence
<220> FEATURE:
<223> OTHER INFORMATION: probe

<400> SEQUENCE: 24
gcggagacag accaactaga agatgagaag tctgctttgc                              40

<210> SEQ ID NO 25
<211> LENGTH: 40
<212> TYPE: DNA
<213> ORGANISM: Artificial Sequence
<220> FEATURE:
<223> OTHER INFORMATION: probe

<400> SEQUENCE: 25
gcaaagcaga cttctcatct tctagttggt ctgtctccgc                              40

<210> SEQ ID NO 26
<211> LENGTH: 30
<212> TYPE: DNA
<213> ORGANISM: Artificial Sequence
<220> FEATURE:
<223> OTHER INFORMATION: probe

<400> SEQUENCE: 26
tctagttggt ctgtctccgc cccccccccc                                         30
```

<210> SEQ ID NO 27
<211> LENGTH: 40
<212> TYPE: DNA
<213> ORGANISM: Artificial Sequence
<220> FEATURE:
<223> OTHER INFORMATION: probe

<400> SEQUENCE: 27
cccccccccc cccccccccc gcaaagcaga cttctcatct        40

<210> SEQ ID NO 28
<211> LENGTH: 30
<212> TYPE: DNA
<213> ORGANISM: Artificial Sequence
<220> FEATURE:
<223> OTHER INFORMATION: probe

<400> SEQUENCE: 28
cccccccccc gcggagacag accaactaga        30

<210> SEQ ID NO 29
<211> LENGTH: 40
<212> TYPE: DNA
<213> ORGANISM: Artificial Sequence
<220> FEATURE:
<223> OTHER INFORMATION: probe

<400> SEQUENCE: 29
agatgagaag tctgctttgc cccccccccc cccccccccc        40

NUCLEIC ACID DETECTION IN CYTOPLASM

BACKGROUND OF THE INVENTION

1. Field of the Invention

This invention relates to a method for the detection of a target nucleic acid in the cytoplasm of a living cell. More specifically, it relates to a method for the detection of a target nucleic acid existing in the cytoplasm of a living cell through hybridization by using probes labeled with fluorescent dyes.

2. Related Background Art

Hybridization is known as one of the methods to detect a nucleic acid having a specified base sequence (hereafter referred to as "target nucleic acid"). This method employs an oligonucleotide probe having a base sequence capable of hybridizing to the target nucleic acid as a detection probe to form a hybrid, and performs detection of the target nucleic acid by detecting the hybrid through various detection means.

Hybridization methods in the prior art, however, suffer from the drawbacks described below. Thus it will be difficult to apply them to detecting a target nucleic acid in the cytoplasm of a living cell. In other words, when a detection probe is introduced into the cytoplasm, it will rapidly move to the nucleus. This makes it difficult to allow the probe to form a hybrid with the target nucleic acid existing in the cytoplasm. In addition, the detection probe, which has been introduced into the cytoplasm, or the hybrid between the detection probe and the target nucleic acid is rapidly digested by various kinds of nuclease existing in the cytoplasm, which renders the detection of the target nucleic acid difficult.

SUMMARY OF THE INVENTION

The present inventors have discovered that a detection probe having a specified structure does not rapidly move to nucleus when introduced into the cytoplasm of a living cell and that it is not easily digested by nuclease, and thus have accomplished this invention. Specifically, when the detection probe having the specified structure is introduced into the cytoplasm, the probe does not readily move into the nucleus; nor is it readily digested by the nuclease. The probe forms a hybrid with a target nucleic acid existing in the cytoplasm, and the hybrid will be detectable without being subjected to digestion by the nuclease. Accordingly, when such a detection probe is used, the method for the detection of a target nucleic acid existing in the cytoplasm of a living cell (hereafter referred to as "the detection method of this invention) will be attained.

Specifically, the detection probe to be used in the method of this invention has the following characteristics: it is an oligonucleotide probe having a base sequence capable of hybridizing to the specified base sequence of a target nucleic acid; it is provided with a molecule that prevents the movement of the oligonucleotide into nucleus through nuclear membrane pores, and preferably, blocks the digestion of the oliginucleotide by nuclease; and it is provided with a fluorescent label that only allows the detection of the hybrid with the target nucleic acid.

Preferably, the detection probe to be used in the detection method of this invention is a pair of probes comprising two types of oligonucleotide probe which are respectively bound to an energy donor fluorescent dye (also referred to as "donor fluorescent dye" or simply as "donor" hereafter) and an energy acceptor fluorescent dye (also referred to as "acceptor fluorescent dye" or simply as "acceptor" hereafter) such that fluorescence resonance energy transfer (also referred to as "FRET" hereafter) can take place to allow the detection of only the hybrid with the target nucleic acid; each of the probes is an oligonucleotide probe having a base sequence capable of hybridizing to the target nucleic acid adjacently with each other with the result of forming the hybrid.

Specifically, this invention is characterized in that it employs the detection probe having such a specified structure, and the following detection method is provided in accordance with the invention:

A method for detecting a target nucleic acid existing in cytoplasm of a living cell, the method comprising:

introducing into the cytoplasm, a detection probe bound to a nuclear membrane unpermeable molecule via a linker and labeled with a fluorescent dye, the probe having a base sequence capable of hybridizing to the target nucleic acid;

forming a hybrid between the target nucleic acid and the probe; and determining any change in fluorescence of the fluorescent dye due to formation of the hybrid.

According to this invention, there is further provided:

The method for detecting a target nucleic acid existing in the cytoplasm of a living cell as described above, wherein the detection probe comprises a first probe member and a second probe member, the first and second probe members have base sequences capable of hybridizing to the target nucleic acid adjacently with each other, the first probe member is labeled with an energy donor fluorescent dye and the second probe member is labeled with an energy acceptor fluorescent dye, and the change in fluorescence of the fluorescent dyes is fluorescence resonance energy transfer from the fluorescent dye of the first probe member to the fluorescent dye of the second probe member.

This invention provides the detection method as described above wherein the nuclear membrane unpermeable molecule is preferably at least one member selected from the group consisting of proteins, sugars, beads, and metal particles that have sizes sufficient so as not to pass through the nuclear membrane pores. More preferably, the protein includes streptavidin and avidine. Also, the sugar includes dextran.

In the detection method described above, the detection probe may further contain a molecule that blocks digestion of an oligonucleotid by nuclease (hereafter referred to as "nuclease-blocking molecule" and that is bound to the detection probe via a linker. Here, it is preferred that the nuclease-blocking molecule be identical with the nuclear membrane unpermeable molecule. This means that the nuclear membrane unpermeable molecule for use in the invention is provided with the function of a nuclease-blocking molecule.

This invention provides the detection method as described above wherein the nuclear membrane unpermeable molecule is characterized in that it is preferably at least one member selected from the group consisting of proteins, sugars, beads, and metal particles. More preferably, the protein includes streptavidin and avidine. Also, the sugar includes dextran.

In the detection method described above, the detection probe is preferably an oligonucleotide comprising from 10 to 20 bases.

Further, in the detection method described above the target nucleic acid to be detected is preferably messenger RNA (mRNA).

Since the detection method of the invention is highly specific, it will become possible to detect only the target nucleic acid with high sensitivity despite that a large number of nucleic acids of other kinds are present in a living cell.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 2A shows a DD image obtained when the Bodipy493/503-labeled oligo DNA probe (D2F) was introduced into the cell; FIG. 2B shows an AA image obtained when the Cy5-labeled oligo DNA probe (A2F) was introduced into the cell; FIG. 2C shows a DD image obtained when the Bodipy 493/503-labeled oligo DNA probe bound to streptavidin (D2FB/streptavidin) was introduced into the cell; and FIG. 2D shows an AA image obtained when the Cy5-labeled oligo DNA probe bound to streptavidin (A2FB/streptavidin) was introduced into the cell.

FIG. 5A shows a DD image and FIG. 5B shows a DA image. The 40 mer target RNA was also injected after 10 minutes. FIG. 5C shows the later DD image and FIG. 5D shows the later DA image. The length of the bar in FIG. 5A represents 20 μm.

FIG. 6A shows a DD image and FIG. 6B shows a DA image. The 40mer non-target DNA was also injected after 10 minutes. FIG. 6C shows the later DD image and FIG. 6D shows the later DA image. The length of the bar in FIG. 6A represents 20 μm.

FIG. 8A shows the state after 1 minute; FIG. 8B shows the state after 5 minutes; FIG. 8C shows the state after 10 minutes; and FIG. 8D shows the state after 20 minutes. The length of the bar in FIG. 8A represents 20 μm.

FIG. 9A shows a DD image; FIG. 9B shows a DA image; FIG. 9C shows an AA image; and FIG. 9D shows a phase contrast (Ph) image. The length of the bar in FIG. 9A represents 20 μm.

FIG. 10A shows the state after 5 minutes, and FIG. 10B shows the state after 20 minutes.

FIG. 11A shows the state after 1 minute; FIG. 11B shows the state after 5 minutes; FIG. 11C shows the state after 10 minutes; and FIG. 11D shows the state after 20 minutes. The length of the bar in FIG. 11A represents 20 μm.

FIG. 13A shows the state after 1 minute; FIG. 13B shows the state after 5 minutes; FIG. 13C shows the state after 10 minutes; FIG. 13D shows the state after 20 minutes. The length of the bar in FIG. 13A represents 20 μm.

FIG. 14A shows the state after 1 minute; FIG. 14B shows the state after 5 minutes; FIG. 14C shows the state after 10 minutes; and FIG. 14D shows the state after 20 minutes. The length of the bar in FIG. 14A represents 20 μm.

FIG. 15A shows a DD image; FIG. 15B shows a DA image; FIG. 15C shows an AA image; and FIG. 15D shows a Ph image.

FIGS. 16A and 16B are pseudocolor representations of the ratio image obtained by dividing the DA image by the DD image in the experiment of FIGS. 15A–15D. FIG. 16A shows the state after 5 minutes, and FIG. 15B shows the state after 20 minutes.

DESCRIPTION OF THE PREFERRED EMBODIMENTS

This invention will be explained in detail by referring to preferred embodiments.
Outline of the Detection Method of the Invention As an example of the detection method of the invention, an explanation will be made below to the preferable procedure for visualizing and detecting a specified kind of mRNA within a living cell.

Figure 1A:
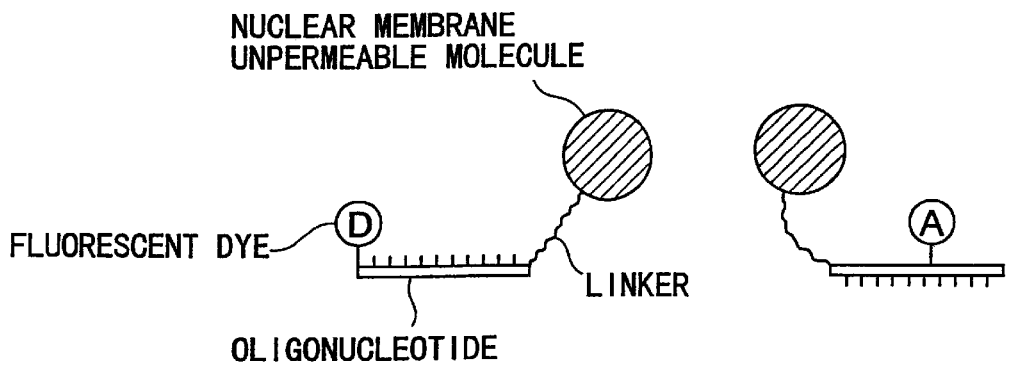
FIG. 1A shows a structure for the probe to be used in this invention.
Figure 1B:
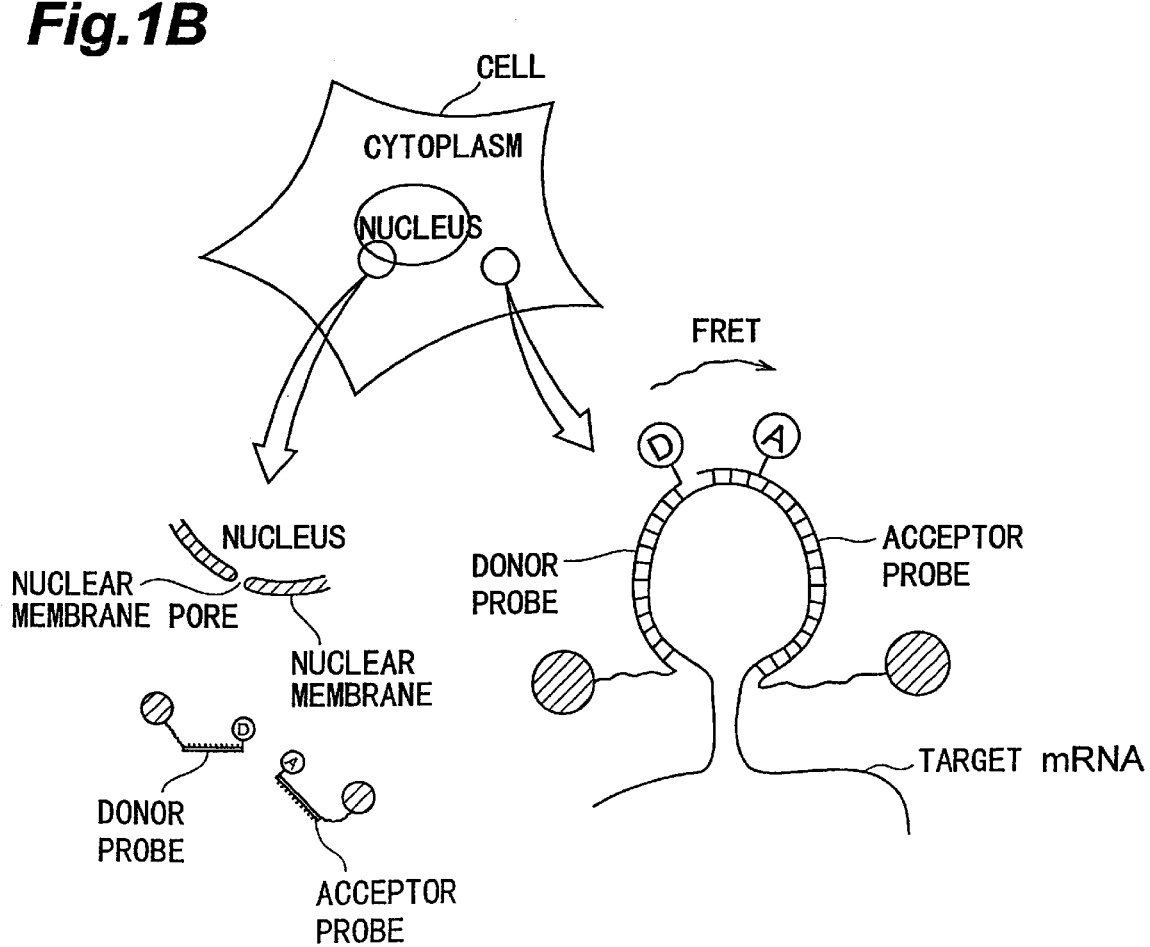
FIG. 1B is a schematic representation of the detection method of the invention.

As FIG. 1 schematically shows, two types of probe for detection are provided and are combined to a pair for use. Each probe comprises three components: (1) an oligonucleotide that hybridizes to target mRNA; (2) a molecule having such a size that does not permeate through the nuclear membrane in a cell; (3) a linker connecting the two. The base sequence of each oligonucleotide constituting a first or a second probe member is a base sequence capable of hybridizing adjacently with each other to the specified site of mRNA which is the object of detection.

mRNA is generally believed to have a complex structure of its own. For this reason, even if the oligonucleotide has a base sequence complementary to the specified site of mRNA, steric hindrance to hybridization may occur at the particular site. This necessitates the selection of the site of mRNA at which the oligonucleotide should hybridize to the target mRNA. Selection of the specified sites is feasible, for example, in the following manner. First, the secondary structure of mRNA is simulated. For example, this can be done by using a commercially available computer program for prediction of the secondary structures of RNAs such as DINsis. In the obtained secondary structure map, a site comprising 30–40 bases centered around the site at which RNA forms a single strand structure (loop) is selected. The site is divided into two segments (each 15–20 bases). Oligonucleotides having base sequences complementary to the respective segments are synthesized. These two segments make up a first oligonucleotide and a second oligonucleotide.

Further, the first and second oligonucleotides are respectively labeled with fluorescent dyes of different types. These two types of fluorescent dye are selected to be a combination such that it causes FRET when they are located at an adequate distance (8 nm or less) with respect to each other: one dye is denoted "donor" and the other denoted "acceptor." The labeling positions of the respective fluorescent dyes on the oligonucleotide are those which allow for the stereostructure such that the two types of fluorescent dye are located at a distance at which they generate FRET when the two types of probe and the target mRNA form a 3-member hybrid. In practice, if the two fluorescent dyes are located within a distance of 20 bases or less on the hybrid, this condition will be met. More specifically, a model experiment has demonstrated that two to four bases efficiently cause FRET. For a general review on FRET, see Lakowicz, J. R. "Principles of Fluorescence Spectroscopy" (1983), Plenum Press, New York.

The first and the second fluorescently labeled oligonucleotides that have been synthesized in the manner described above are mixed, and their fluorescent spectra are measured. Next, the target mRNA is added to this solution, and any change in fluorescent spectrum is observed. If these three forms a hybrid, FRET occurs between the two types of fluorescent dye. The result is that one obtains a fluorescent spectrum where the fluorescent intensity of the donor has decreased and the fluorescent intensity of the acceptor has increased.

Preferably, the above-described manipulations are conducted on each of several kinds of site that are selected on the secondary structure map of mRNA; the degrees of spectral change are compared, and the sites showing large degrees of spectral change are selected. The mRNA to be used in the measurement can be synthesized by in vitro transcription reactions using a plasmid DNA into which has been incorporated the corresponding cDNA.

To accurately evaluate the efficiency of hybridization of the respective sites to the target mRNA, the following is to be done. After each fluorescently labeled oligonucleotide and the target mRNA are mixed in aqueous solution, the oligonucleotide having hybridized to the mRNA and the oligonucleotide not having hybridized to the mRNA are separated by HPLC. The ratio of the oligonucleotide having undergone hybridization is determined from the area ratio of the fluorescent intensities of the respective peaks.

It is also possible to confirm and evaluate the hybridization of each oligonucleotide to the target mRNA in a living cell by "in situ transcription method." Namely, the fluorescently labeled oligonucleotide is incorporated into the living cell. This can be done, for example, by adding the fluorescently labeled oligonucleotide to a medium where the cells are grown and by incubating the medium for a predetermined period. Subsequently, the cells are fixed. Reverse transcription is then conducted on the fixed cells, where the position of the oligonucleotide serves as the initiation site of a primer. If the oligonucleotide is hybridized to the target mRNA, the transcription will take place, thus producing cDNA corresponding to the target mRNA. The synthesized CDNA is then to be detected.

Next, each oligonucleotide is bound via a linker to a molecule having such a size that does not permeate through the nuclear membrane. For example, streptavidin, one kind of protein, can be used as the molecule having such a size that does not permeate through the nuclear membrane; and an oligonucleotide can be used as the linker. In this case, it is preferred that the fluorescently labeled oligonucleotide for hybridization with the target mRNA and the oligonucleotide equipped with the function of a linker be synthesized as a single oligonucleotide. Biotin is coupled to one end of the oligonucleotide. The oligonucleotide labeled with a fluorescent dye and biotin is mixed with streptavidin in aqueous solution to achieve binding of the two. Since streptavidin is tetravalent with respect to biotin in binding, a plurality of fluorescently labeled oligonucleotide molecules may bind to one molecule of streptavidin. To prevent this from occurring, the mixing ratio is set such that streptavidin is present in excess. In practice, the molar ratio of oligonucleotide to streptavidin is desirably 1:4. Donor and acceptor probes are both used in the form of being bound to streptavidin. Therefore, it must be avoided that both of the donor and acceptor oligonucleotides are bound to the same streptavidin, for FRET occurs when the both are bound. The binding reaction between the oligonucleotide and streptavidin is conducted under the conditions where streptavidin is present in excess relative to each of the donor and acceptor oligonucleotides. This ensures that all the oligonucleotides be bound to streptavidin: no free oligonucleotide is present when the donor oligonucleotides premixed with streptavidin are mixed with the acceptor oligonucleotides premixed with streptavidin.

The length of the linker may be such that it effectively causes the relaxation of steric hindrance so that hybridization of the probes described above to the target mRNA in the cell progresses efficiently. Practically, a length of 20 bases or less is desirable. There are no particular limitations for the base sequence of the linker portion; however, one must avoid to use a base sequence that possibly causes hybridization of the target mRNA to other sites or hybridization to other kinds of mRNA. The backbone of the linker portion may employ one that is highly resistant to nuclease, such as S-oligo (deoxysulphonate oligonucleotide).

The two types of probe thus prepared are mixed and introduced into cells. For example, the probes may be injected into the cytoplasm by microinjection.

The fluorescent image of the cell is to be measured. The fluorescent image of the cell is observed with a standard inverted fluorescence microscope. The excitation filter, dichroic filter and fluorescence filter are adequately set to the wavelength of the donor dye and to that of the acceptor dye, respectively. This permits observation of the distribution of the donor probe within the cell, the distribution of the acceptor cell within the cell, and their time-dependent changes. The cells are incubated on a stage of the microscope. Where necessary, among others the temperature is regulated, for example, by the method circulating the culture medium.

Measurement of FRET in a cell can be conducted by determining the ratio of fluorescent intensities in two wavelength regions. Specifically, where the efficiency of FRET at an arbitrary position in the cell is to be determined, the fluorescent intensity (Id) in the wavelength region of donor fluorescence and the fluorescent intensity (Ia) in the wavelength region of acceptor fluorescence are measured at that position when the cell is irradiated with light in the excitation wavelength region of the donor dye; and the ratio (Ia/Id) of the Ia value to the Id value may be determined. The value of Ia/Id represents the efficiency of FRET.

Fluorescent images in two wavelength regions, namely a fluorescent image taken in the wavelength region of the donor fluorescence (referred to as "DD image" throughout the specification) and a fluorescent image taken in the wavelength region of the acceptor fluorescence (referred to as "DA image" throughout the specification) by irradiating the cell with the light in the excitation wavelength region of the donor, are obtained. Imaging of FRET in the cell becomes possible by dividing the DA image by the DD image to obtain an image (referred to as "DA/DD image" throughout the specification unless the term "the ratio image" is used instead).

Measurement of FRET can also be possible through the time-resolved measurement of fluorescence. That is, the cell is irradiated with the light in the excitation wavelength region of a donor dye in a pulse manner, and the decay curve of fluorescence intensity in the wavelength region of the donor fluorescence or in the wavelength region of the acceptor fluorescence is measured. When FRET occurs, it accelerates the rate of the fluorescence decay of the donor and delays the fluorescence decay of the acceptor. Measurement of the rate of fluorescence decay under microscopy can be made, for example, by using a camera with a time-gate function, setting two time zones for measurement within the time period when the fluorescence decay is occurring, and by determining fluorescence intensities in the respective time zones to obtain the ratio of the fluorescence intensities. To effectively detect the formation of hybrids through the time-resolved measurement, fluorescently labeled oligonucleotides may be used that satisfy the conditions disclosed in PCT/JP97/03438.

The detection method of this invention will be explained in detail hereafter.

Target Nucleic Acids

There are no particular limitations for the kind of nucleic acid in cytoplasm that can be detected by the detection method of the invention. Any kind of nucleic acid that can be detected by hybridization methods in the prior art or a derivative thereof may be included. Concretely, there can be mentioned DNA and RNA. Particularly, the RNA includes mRNA.

There are also no particular limitations for the structure possessed by a target nucleic acid that can be detected by the detection method of the invention; and it may be one that has a structure as its portion to which hybridization methods in the prior art are applicable. Namely, the target nucleic acid is the one at least a part of the base sequence of which is known. When the base sequence of a target nucleic acid is unknown, a part or its entire base sequence can be readily determined according to a variety of base sequencing well known in the art. The detection probes that will be discussed below hybridize to such base sequences in a complementary manner. There are also no particular limitations for the number of bases in the base sequence, and it can readily be selected by referring to the conditions known in hybridization methods in the prior art.

The target nucleic acids that can be detected by the detection method of the invention are not limited to those already existing in cytoplasm when the detection probe is introduced into the cytoplasm. The nucleic acids can be detected even if they are produced and come to being within the cytoplasm after the detection probe has been introduced into the cytoplasm.

Detection Probes

The detection probe that can be used in the detection method of the invention has at least the following features: (1) an oligonucleotide structure that has a base sequence capable of hybridizing to at least a part of the base sequence of the target nucleic acid, as is similarly required by the hybridization methods in the prior art; (2) a labeling molecule that only allows the detection of the hybrid formed by hybridization with the target nucleic acid; (3) a nuclear membrane unpermeable molecule that prevents the permeation of an oligonucleotide through nuclear membrane pores; and preferably (4) a nuclease-blocking molecule that prevents an oligonucleotide from being digested by nuclease. Thus, any oligonucleotide probe is usable without any particular limitations provided that it has the above-mentioned features. These features will be explained in more detail hereafter.

1. Oligonucleotide Structure

A. There are no particular limitations for the kind or the base number of base sequence capable of hybridizing to at least a part of the base sequence of the target nucleic acid as explained above. Preferably, applicable are the conditions that may be used in standard hybridization methods. Based on the specified sequence of a target nucleic acid, base sequences complementary thereto may readily be selected. Further, it is also possible to adequately select the complementation depending on the hybridization conditions.

For the detection probe of this invention, optimum hybridization conditions may be set by referring to the temperature of a sample or the concentration of a target nucleic acid existing in the sample; on that basis the base number may be selected. For example, the melting point of a hybrid formed among the oligonucleotide probes and the target nucleic acid increases with increasing numbers of bases of the probes. The hybrid is formed with sufficient high efficiency at room temperature when the base number of the probe is 15, while the efficiency of formation of the hybrid at 37° C. is low. To perform detection at 37° C., it is therefore desirable to use an oligonucleotide having a length of 20 bases or more as the probe. On the other hand, as the base number of the oligonucleotide probe grows greater, the reaction rate by which the probe forms the hybrid with the target nucleic acid becomes lower. Concretely, the time required for the hybridization reaction between DNA probes with 20 bases and the target nucleic acid to be complete is a few times that needed when DNA probes with 15 bases are used. Judging from these factors, the base number of the oligonucleotide probe for use is preferably in the range of from 10 to 50 bases, more preferably in the range of from 15 to 20 bases. If the base number falls short of such range, there will be difficulty of the formation of a sufficiently stable hybrid; on the other hand, if the number exceeds the range, there may be cases where problems arise from various aspects such as preparation of the detection probes, their stability, and the times required for the hybrid formation. Concerning the complementation of the base sequences between the detection probes and the target nucleic acid, the most preferred is a sequence with complete complementation. In the case of an oligonucleotide, probe for detection having no complementation in at least a portion thereof, the melting point of the hybrid with the target nucleic acid experiences a decrease as compared to the one with complete complementation.

B. There are no particular limitations for the other structure of the detection probe having an oligonucleotide structure with the base sequence as explained in A above.

C. where necessary, the detection probe can possibly be used such that hybrids are formed at a plurality of sites in the target nucleic acid. For example, the sites may be a position near one end of the target nucleic acid, a position near the middle point thereof, and a position near the other end thereof.

2. Labeling Molecules

The detection method of this invention detects a target nucleic acid in cytoplasm by detecting the hybrid of the target nucleic acid and detection probes. Particularly, in the invention it will be possible to detect the target nucleic acid existing in the cytoplasm of a living cell; for this reason, it is preferred that the invention can detect only the hybrid being formed without the need of its separation. Therefore, the labeling molecules preferably utilize the phenomenon that results only when they are hybridized to the target nucleic acid adjacently with each other. There are no particular limitations for such a phenomenon, and a variety of phenomena that are well known in the prior art may be relied upon. Especially, in this invention it is preferable to utilize fluorescence phenomena in view of their high detection sensitivity, means for their easy measurement, and the like. Specifically, the phenomenon that only results from the molecules' being hybridized is preferably one that utilizes the phenomenon, "FRET." Such labeling by fluorescence will be made possible by labeling a pair of single strand oligonucleotide probes with an energy donor fluorescent dye and an energy acceptor fluorescent dye. In this regard, there are no particular limitations for the donor and acceptor molecules that can cause FRET; and one skilled in the art finds it easy to adequately select among the already known combinations of fluorescent dyes. Concretely mentioned as a donor are fluorescent dyes of the Bodipy type (4,4-difluoro-4-bora-3a,4a-diaza-S-indacene, Molecular Probe), of the fluorescein type, and of the Rhodamine type. Mentioned as an acceptor are fluorescent dyes of the indocyanine type, and of the Rhodamine type. For the combination of donor and acceptor molecules that can preferably be used in this invention, there may be mentioned a Bodipy/indocyanine type. Preferable individual fluorescent dyes are Bodipy493/503 as the donor and Cy5 as the acceptor. This is because the fluorescence spectrum of the former is almost separated from the fluorescence spectrum of the latter at wavelength.

3. Nuclear Membrane Unpermeable Molecules

The detection probe explained in 2 above has a molecule that prevents the probe in the cytoplasm from permeating into the nucleus through nuclear membrane pores. Particularly, as the molecule that does not pass through nuclear membrane pores by diffusion, a molecule can be selected such that it is large sufficient for the sizes of the nuclear membrane pores. Furthermore, there are no particular limitations for the components that comprises the nuclear membrane unpermeable molecule, and a variety of biological and synthetic components can be used. The biological components or the components based thereon include proteins and dextran. The synthetic components include beads made of various constituents and metal particles such as colloidal gold.

There are no particular limitations to the method for binding a nuclear membrane unpermeable molecule to the oligonucleotide explained in 1. above, and binding methods ordinarily known in the art are applicable. Specifically, when a protein is selected as the nuclear membrane unpermeable molecule, binding is preferably done through reaction with amino acid residues (e.g., amino or carboxyl) within the protein. Specific binding between biotin and streptavidin or avidine may also be utilized. Namely, biotin is incorporated into one end of an oligonucleotide or within a strand thereof in synthesis, avidine or streptavidin is mixed with the product. Through this manipulation the oligonucleotide containing biotin is allowed to bind to avidine or streptavidin. The oligonucleotide containing biotin can readily be synthesized on a DNA synthesizer. Further, the nuclear membrane unpermeable molecule is bound to the oligonucleotide via a linker of appropriate length. Such linkers include oligonucleotide derivatives and oligopeptides.

4. Nuclease-Blocking Molecules

Preferably, the detection probe explained in 2 above has a nuclease-blocking molecule that prevents an oligonucleotide from being digested by nuclease. Although there are no particular limitations for the blocking, this invention preferably employs such molecules that prevent a substrate from approaching to its binding site on an enzyme (nuclease) by virtue of steric hindrance. Furthermore, there are no particular limitations for the components that comprise the nuclease-blocking molecule, and a variety of biological and synthetic components can be used. The biological components or the components based thereon include proteins and dextran. The synthetic components include beads made of various constituents and metal particles such as colloidal gold.

There are no particular limitations to the method for binding a nuclease-blocking molecule to the oligonucleotide explained in 1 above, and binding methods ordinarily known in the art are applicable. Specifically, when a protein is selected as the nuclease-blocking molecule, binding is preferably done through reaction with amino acid residues (e.g., amino or carboxyl) within the protein. Specific binding between biotin and streptavidin or avidine may also be utilized. Namely, biotin is incorporated into one end of an oligonucleotide or within a strand thereof in synthesis, avidine or streptavidin is mixed with the product. Through this manipulation the oligonucleotide containing biotin is allowed to bind to avidine or streptavidin. The oligonucleotide containing biotin can readily be synthesized on a DNA synthesizer. Further, where necessary, the nuclease-blocking molecule is bound to the oligonucleotide via a linker of appropriate length. Mentioned as such a linker are oligonucleotide derivatives and oligopeptides. As used herein, the oligonucleotide includes D-oligo (deoxyoligonucleotide) and S-oligo.

Particularly in this invention, it is preferred that the nuclear membrane unpermeable molecule explained above be a nuclease-blocking molecule at the same time. That is, the nuclear membrane unpermeable molecule prevents the detection probes from permeating through nuclear membrane pores, while at the same time, it prevents the detection probes or the hybrids of the detection probes and the target nucleic acid from enzymatic digestion. In such cases, it is preferred that the nuclear membrane unpermeable molecule effectively exerting the two kinds of inhibition (synergic nuclease-blocking molecule) be provided with a linker of appropriate type and length. For the type of linker, concretely mentioned are oligonucleotides and oligopeptides, the former of which are particularly preferred. If the linker is too long, it will not produce steric hindrance that prevents the enzymatic reaction, for which reason its length is preferably shorter than about 20 bases. On the other hand, if the linker is too short, its steric hindrance will obstruct the formation of a stable hybrid with the target nucleic acid. Consequently, the kind and length of a suitable linker can be adequately selected based on steric molecular models, molecular model calculation programs, and the like.

Detection Methods

According to a preferred embodiment of this invention, the detection probes explained above are introduced into the cytoplasm and allowed to hybridize to the target nucleic acid, forming the hybrid; at that time, the probes are irradiated with the excitation light of the donor fluorescent dye bound to the probe to cause FRET, and fluorescence from the acceptor fluorescent dye due to the FRET is observed. That is, the donor fluorescent dyes of the detection probes that have not formed hybrids are simultaneously irradiated, but FRET does not occur between the acceptor fluorescent dyes of the detection probes that have not formed hybrids and the donor fluorescent dyes. Thus, fluorescence from the acceptor fluorescent dyes can not be observed. Consequently, the fluorescence from acceptor fluorescent dye means the presence of a hybrid, namely the presence of the target nucleic acid.

Moreover, there are no particular limitations for the detection device to be used in the detection method of this invention, and it may be sufficient provided that it can excite the donor fluorescent dye and can measure fluorescence of the acceptor fluorescent dye as well. Specifically the use of a fluorescence microscope is mentioned. There are also no particular limitations for the method of measurement, and mentioned are the method relying on the measurement of fluorescence intensity and the method relying the time-resolved measurement.

There are also no particular limitations for the method of introducing the detection probes into the cytoplasm, and introduction methods well known in the prior art may be used. Concretely mentioned are microinjection and the introduction method which relies on as a carrier, a transfection reagent such as lipofectoamine.

In what follows, the detection method of this invention will be explained in more detail based on the example where mRNA of human c-fos gene was actually detected in Cos7 cells; however, the invention is not to be limited to the particular example. Here, a combination of Bodipy493/503 as the donor and Cy5 as the acceptor was used.

EXAMPLES

Production Example 1

Preparation of Fluorescently Labeled Oligodeoxynucleotide Probes

1. Prediction of Secondary Structure of c-fos mRNA

A base sequence of human c-fos cDNA was searched in the DNASIS database (Hitachi Software Engineering). PolyA tail was added to the base sequence to prepare a c-fos mRNA sequence. The DNASIS software (Hitachi Software Engineering) was used on this sequence for simulation of the secondary structure of c-fos mRNA. From the resulting secondary structure map, there were selected four domains that showed a loop structure (single stranded structure), and a 40mer site containing the loop structure was selected for each domain. These sites were base Nos. 206–245, 657–696, 898–937 and 1659–1698.

2. Synthesis of Oligodeoxynucleotides

Each of the four selected sites was divided into two 20mer halves, and oligodeoxynucleotides (referred to as "oligo DNA(s)" throughout the specification) complementary to the respective sequences were synthesized.

D1: Oligo DNA with base sequence complementary to 206–225

5'-XGAACATCATCGTGGCGGTTA-3'

A1: Oligo DNA with base sequence complementary to 226–245

5'-TAGTCTGCGTTGAAGCYCCGA-3'

D2: Oligo DNA with base sequence complementary to 657–676

5'-XTCTAGTTGGTCTGTCTCCGC-3'

A2: Oligo DNA with base sequence complementary to 677–696

5'-GCAAAGCAGACTTCTCYATCT-3'

D3: Oligo DNA with base sequence complementary to 898–917

5'-XTCCGGGGTGGCAACCTCTGG-3'

A3: Oligo DNA with base sequence complementary to 918–937

5'-GGGTGAAGGCCTCCTCYAGAC-3'

D4: Oligo DNA with base sequence complementary to 1659–1678

5'-XAAGGACTAAGGAGAAAGAGA-3'

A4: Oligo DNA with base sequence complementary to 1679–1698

5'-AGATTAGTTAATGCTAYTGAG-3'

The synthesis of each of these oligo DNAs was carried out according to the β-cyanoethyl amidite method, using a Model 394 (Perkin Elmer Applied Biosystems) or an Expeptide Model 8909 (Perspective). Here, "X" was 6-(trifluoroacetylamino)hexyl-(2-cyanoethyl)-(N,N-diisopropyl)-phosphoroamidite (TFAc hexanolamine linker, Perkin Elmer, Japan: Cat. No. 400808), and "Y" was Uni-Link Amino Modifier (CLONTECH, Code No. CL5190-1).

The resulting crude product was analyzed by DEAE-HPLC and the main peak fractions were recovered. The retention times were 20–30 minutes. The aliquots were desalted and then lyophilized.

DEAE-HPLC (anion-exchange) conditions
Solvent A: 0.2 M $HCOONH_4$, 20% $CH_3CN$
Solvent B: 1.0 M $HCOONH_4$, 20% $CH_3CN$
Column: TSK-gel DEAE-2WS; 4.6×250 mm (Tosoh)
Flow rate: 0.8 ml/min
Temperature: 40° C.
B gradient: 35–85% (20 min)

3. Fluorescence Labeling of Oligodeoxynucleotides
3-1. Labeling with Bodipy493/503

The fluorescent dye Bodipy493/503 was conjugated to the "X" of each oligo DNA of D1, D2, D3 and D4 by the following method.

Separately there were dissolved 2.5 mg of sodium N-hydroxysulfosuccinimide in 30 μl of sterilized water and 5 mg of 1-ethyl-3-(3-dimethylaminopropyl)-carbodiimide hydrochloride in 50 μl of sterilized water. Bodipy493/503 propionic acid, 1 mg, (Molecular Probes) dissolved in 50 μl of DMF was mixed therewith for reaction at room temperature for 30 min. The resulting solution was mixed with a solution of the oligo DNA, which was prepared by dissolving dried oligo DNA in 300 μl of 0.5 M $NaHCO_3/Na_2HCO_3$ (pH 9.0), and the mixture was allowed to react overnight with light exclusion. The reaction solution was applied to gel filtration and the unreacted dye was eliminated. Analysis was performed by reversed phase HPLC, and the peak at 25–35 minutes was recovered.

Reversed phase HPLC conditions
Solvent A: 0.05 M TEAA (triethylammonium acetate), 5% $CH_3CN$
Solvent B: 0.05 M TEAA, 40% $CH_3CN$
Column: CAPCELL PAK C18; 6×250 mm (Shiseido)
Flow rate: 1.0 ml/min
Temperature: 40° C.
B gradient: 30–80% (20 min)

The samples were lyophilized and stored. Just prior to use, they were dissolved in DEPC-water (diethyl pyrocarbonate) and then diluted with 1×SSC solution; and their absorption spectra were measured. The Bodipy493/503 labeling yields (Bodipy 493/503/oligo DNA) were determined by the ratios of the 260 nm absorbance and the 504 nm absorbance. The Bodipy493/503/oligo DNA values were 0.8–0.9 (molar ratio).

The resulting Bodipy493/503-labeled oligo DNAs were as follows.

```
D1F:  5'-(Bodipy493/503)GAACATCATCGTGGCGGTTA-3'

D2F:  5'-(Bodipy493/503)TCTAGTTGGTCTGTCTCCGC-3'

D3F:  5'-(Bodipy493/503)TCCGGGGTGGCAACCTCTGG-3'

D4F:  5'-(Bodipy493/503)AAGGACTAAGGAGAAAGAGA-3'
```

3-2. Labeling with Cy5

Cy5 was conjugated to "Y" of each oligo DNA of A1, A2, A3 and A4 by the following method.

FluoroLink Cy5 Mono Reactive Dye (Amersham Pharmacia Biotech) was dissolved in 100 μl of sterilized water, and this was then mixed with an oligo DNA dissolved in 200 μl of a 0.5 M $NaHCO_3/Na_2HCO_3$ buffer (pH 9.0) and was allowed to react overnight with light exclusion. The reaction solution was applied to gel filtration and the unreacted Cy5 was eliminated, after which analysis was performed by reversed phase HPLC, and the peak at 20–25 minutes was recovered.

Reversed phase HPLC conditions:
Solvent A: 0.05 M TEAA, 5% $CH_3CN$
Solvent B: 0.05 M TEAA, 40% $CH_3CN$
Column: CAPCELL PAK C18; 6×250 mm (Shiseido)
Flow rate: 1.0 ml/min
Temperature: 40° C.
B gradient: 15–65% (20 min)

The samples were lyophilized and stored. Just prior to use, they were dissolved in DEPC-water and then diluted with 1×SSC buffer; and their absorption spectra were measured. The Cy5 labeling yields (Cy5/oligo DNA) were determined by the ratios of the 260 nm absorbance and the 649 nm absorbance. The Cy5/oligo DNA values were 0.9–1.0 (molar ratio).

The resulting Cy5-labeled oligo DNAs were as follows.

```
A1F:  5'-TAGTCTGCGTTGAAGC(Cy5)CCGA-3'

A2F:  5'-GCAAAGCAGACTTCTC(Cy5)ATCT-3'

A3F:  5'-GGGTGAAGGCCTCCTC(Cy5)AGAC-3'

A4F:  5'-AGATTAGTTAATGCTA(Cy5)TGAG-3'
```

Preparation Example 2

Synthesis of c-fos RNA c-fos RNA was synthesized by in vitro transcription reactions. Human c-fos DNA was obtained from the Riken Gene Bank in the form of a pSPT plasmid containing the full-length of c-fos cDNA (pSPT-cFos). The pSPT-cFos was treated with restriction enzyme EcoRI to cut out a c-fos DNA (2.1 kb). The c-fos DNA fragment was then incorporated into the EcoRI site of pBluescript KII(+) plasmid (Stratagene). The obtained plasmid (pBluescript-cFos) was linearized by treatment with restriction enzyme SmaI, and then used as a template for in vitro transcription reactions. The in vitro transcription reactions driven by T3 RNA polymerase were performed using a T3 MEGAscript kit (Ambion). The reaction solution was treaed with phenol/chloroform to extract the synthesized RNA from the solution containing proteins, followed by treatment with ethanol to precipitate and recover the synthesized RNA.

Example 1

Assay for Hybridization of Fluorescently Labeled Probes to c-fos RNA

1. Fluorescently Labeled Oligo DNA Probes (Fluorescently Labeled Probes)

Each pair of oligonucleotides, D1F/A1F, D2F/A2F, D3F/A3F and D4F/A4F was used as a pair of fluorescently labeled probe for each site that showed a loop structure (single stranded structure) in the secondary structure prediction map for c-fos mRNA. These had base sequences complementary to the 206–225 site (D1F) and 226–245 site (A1F), the 657–676 site (D2F) and 677–696 site (A2F), the 898–917 site (D3F) and 918–937 site (A3F) and the 1659–1678 site (D4F) and 1679–1698 site (A4F) of c-fos mRNA, respectively. Upon forming a 3-member hybrid of each donor probe (Bodipy493/503-labeled oligo DNA) and acceptor probe (Cy5-labeled oligo DNA) with the c-fos RNA, the hybrid takes a form in which four nucleotides exist between the nucleotide to which are bound Bodipy493/503 and Cy5 linked, respectively.

2. Measurement of Fluorescence Spectra

D1F and A1F were mixed in 1×SSC buffer each at a $1×10^{-6}$ M concentration, and the fluorescence spectrum was measured. The fluorescence spectrum was measured in the range of from 500 to 750 nm using an F4500 fluorescence spectrophotometer (Hitachi), with excitation at 480 nm.

The resulting spectrum has a peak near 514 nm. This corresponds to the fluorescence peak of Bodipy493/503. Little fluorescence was detected at 650–700 nm, where the fluorescence of Cy5 appears. c-fos RNA was then added to give a concentration of $1×10^{-6}$ M (D1F:A1F:c-fos RNA= 1:1:1 (molar ratio)). After reaction at room temperature for 15 min, the fluorescence spectrum was measured. The same experiment was carried out for D2F/A2F, D3F/A3F and D4F/A4F, respectively. When the pair of D2F/A2F was used as the fluorescently labeled probes, addition of the c-fos RNA resulted in a significant change in the spectrum. That is, the peak at 514 nm (fluorescence of Bodipy493/503) decreased and fluorescence with a peak at 668 nm (fluorescence of Cy5) appeared. The ratio of the fluorescence intensity at 668 nm and the fluorescence intensity at 514 nm was 0.015 with the probe alone, and 0.55 with the addition of c-fos RNA. A similar change was observed when D1/A1F was used, but the change was smaller. When D3F/A3F and D4F/A4F were used, little change occurred in the spectrum by adding of c-fos RNA. These results are summarized in the following table.

TABLE 1

Ratio of Fluorescence Intensity at 514 nm (I(514)) and Fluorescence Intensity at 668 nm (I(668)) [I(668)/I(514)] in the Fluorescence Spectra:

| fluorescently labeled probe types | probes alone (before addition of c-fos RNA) | after addition of c-fos RNA |
|---|---|---|
| D1F/A1F | 0.015 | 0.15 |
| D2F/A2F | 0.015 | 0.55 |
| D3F/A3F | 0.015 | 0.08 |
| D4F/A4F | 0.015 | 0.09 |

The decrease in Bodipy493/503 fluorescence intensity and increase in Cy5 fluorescence intensity after addition of the c-fos RNA indicates hybridization of the two types of fluorescently labeled probes to the c-fos RNA occurred, resulting in FRET from Bodipy493/503 to Cy5. Based on these results, the 657–696 site (probe: D2F/A2F) was selected as the region for hybridization of oligonucleotides to c-fos RNA.

3. Confirmation of Hybridization Between c-fos RNA and Fluorescently Labeled Probes by HPLC In order to confirm hybridization of D2F and A2F to c-fos RNA, each of the fluorescently labeled probes was mixed with c-fos RNA in 1×SSC solution and then used for an experiment whereby the c-fos RNA-hybridized probes and non-hybridized free probes were separated by high-performance liquid chromatography (HPLC). D2F or A2F and c-fos RNA were mixed in 1×SSC (pH 7.0) solution at a molar ratio of 1:1 (2 µM each) and allowed to stand at room temperature for 20 min, and then analyzed by high-performance liquid chromatography (HPLC) using an ion-exchange column.
Column: DEAE-NPR (Tosoh)
Temperature: 25° C.
Flow rate: 1 ml/min
Mobile phase: 10 mM Tris-HCl, pH 9.5, 1 mM EDTA
Gradient: NaCl, 0.3–1 M (10 min)
Detection: ultraviolet absorption (260 nm)
Fluorescence detection: 475 nm excitation/515 nm fluorescence 650 nm excitation/667 nm fluorescence The free probes were eluted at 3.5–4 min, and the c-fos RNA eluted at 6.9–7.1 minutes. Upon measuring the elution pattern for D2F by Bodipy493/503 fluorescence, peaks were observed at the free oligo DNA position and the c-fos RNA position. Based on the area integration values for the peaks, the ratio of the c-fos RNA to the coeluted D2F probe was 76%. When the Cy5 fluorescence was determined in the same manner for the A2F elution pattern, 43% of A2F was eluted at the c-fos RNA position. These results indicate that 76% of D2F and 43% of A2F hybridized to c-fos RNA when each probe was mixed with c-fos RNA at room temperature at a molar ratio of 1:1.

4. Effect of Probe Length on Hybridization

The effect of the fluorescently labeled probe length on hybridization at 37 ° C. was investigated. A pair of the 20mer D2F and A2F and a pair of a 15mer donor probe (Bodipy493/503-labeled oligo DNA) having the base sequence complementary to the 662–676 site (D5F) and a 15mer acceptor probe (Cy5-labeled oligo DNA) having the base sequence complementary to the 677–691 site (A5F) of c-fos mRNA were used.

The fluorescently labeled oligo DNAs used were the following. The synthesis and purification were carried out by the method described above.
D5F: 5'-(Bodipy493/503)TCTAGTTGGTCTGTC-3'

A5F: 5'-GCAGACTTCTC(Cy5)ATCT-3'

The D2F/A2F pair were mixed in 1×SSC buffer at $1\times10^{-6}$ M concentration each, and the fluorescence spectrum was measured. c-fos RNA was then added thereto to give a concentration of $1\times10^{-6}$ M (D2F:A2F:c-fos RNA=1:1:1 (molar ratio)). The same experiment was carried out for the D5F/A5F pair. These hybridization tests were repeated at 37° C. In all cases, hybridization was completed within 5–15 min. The change in the fluorescence spectrum after 15 min at room temperature was larger when D2F/A2F were used than when D5F/A5F were used. Results are summarized in Table 2.

The ratio of the fluorescence intensity at 668 nm (I(668)) and the fluorescence intensity at 514 nm (I(514)) represents the ratio of the fluorescently labeled probes that hybridizes to the target nucleic acid (c-fos RNA). The ratio of hybridizing probes was larger when D2F/A2F were used than when D5F/A5F were used. When the temperature was raised from room temperature to 37° C., the ratio of hybridizing probes decreased in both cases. However, the decrease was relatively small for D2F/A2F, while it was considerable for D5F/A5F. Thus, the 20mer was shown to be preferable for use as hybridization probes in living mammalian cells.

TABLE 2

| probe length | temperature | I(668 nm)/I(514 nm) |
|---|---|---|
| 15 mer/20 mer | room temperature/37° C. | 0.15 (in the absence of the target c-fos RNA |
| 15 mer | room temperature | 0.40 |
| 15 mer | 37° C. | 0.22 |
| 20 mer | room temperature | 0.51 |
| 20 mer | 37° C. | 0.42 |

Example 2
Assay for Hybridization of Fluorescently Labeled Probes to c-fos mRNA in Cells
1. Introduction of Fluorescently Labeled Probes Into Cells by Injection and Observation of Cells Under a Fluorescence Microscope The D2F probe and A2F probe were mixed in sterilized water at $1\times10^{-5}$ M concentration each, and a mixed solution of fluorescently labeled probes of the two types was introduced into Cos7 cells by microinjection.

Cos7 cells that had been plated for half a day in a dish with a cover glass on the bottom (P35G-O-14-C, MatTek Corp.) were used in the experiment. Just prior to the experiment, the culture solution was removed, and the cells were washed 3 times with HBSS solution and then observed with an inverted fluorescence microscope. The temperature of the cells on the microscope stage was controlled by circulating HBSS solution at 37° C. Microscope: Carl Zeiss Axiovert 135TV, objective lens: 40× Plan-Neofluar (phase contrast, NA=0.75, Model No. 4403519902)

Microinjection was performed using an Eppendorf Micromanipulator 5171 or an Eppendorf Transjector 5246 Plus/BASIC, with a femtotip (Eppendorf). To minimize photobleaching during the measurement, the excitation light was attenuated with a 3% ND filter.
Excitation light source: Superhigh pressure mercury lamp (Model No. L4002)
Filters:
Bodipy493/503 fluorescence image (DD image)
Excitation filter: BP450-490, dichroic mirror: FT510
Barrier filter: BP515-565
Cy5 fluorescence image (AA image)
Excitation filter: BP575-625, dichroic mirror: FT645
Barrier filter: BP660-710

The fluorescence images were taken with a cooled CCD camera (Hamamatsu Photonics: C4880) and transferred into an image processing and analysis apparatus (Hamamatsu Photonics: ARGUS-50).

Figure 2A:
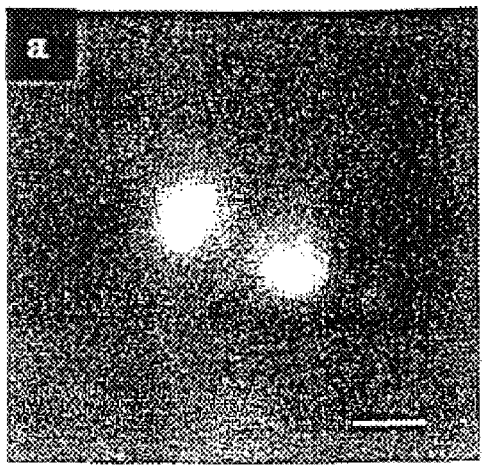
FIGS. 2A–2D are a set of fluorescence micrographs showing fluorescence images of a cell 10 minutes after introduction of a pair of fluorescently labeled probes into a Cos7 cell by microinjection.
Figure 2B:
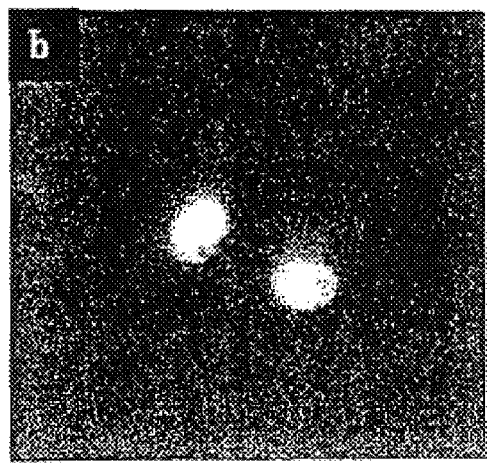

Most of both fluorescently labeled probes (D2F, A2F), which were introduced into the cytoplasm by injection, moved to and accumulated in the nucleus within 10 min (FIG. 2(a),(b)).
2. Distribution of Streptavidin-bound Oligo DNAs in Cells Oligo DNAs each doubly labeled with a fluorescent dye and biotin were synthesized by the following procedure.

5'-XTCTAGTTGGTCTGTCTCCGCV-3'

5'-WGCAAAGCAGACTTCTCYATCT-3'

"X" is TFAc hexanolamine linker (Perkin Elmer, Japan), "Y" is Uni-Link Amino Modifier (CLONTECH), "V" is Biotin ON CPG (CLONTECH), and "W" is Biotin amidite (Perkin Elmer Biosystems). The synthesis and purification were carried out by the method described above. The above-mentioned method was used to bind Bodipy493/503 to "X" and Cy5 to "Y" to obtain the following oligo DNAs doubly labeled with the fluorescent dyes and biotin.

D2FB:
5'-(Bodipy493/503)TCTAGTTGGTCTGTCTCCGC(Biotin)-3'

A2FB:
5'-(Biotin)GCAAAGCAGACTTCTC(Cy5)ATCT-3'

These fluorescent/biotin-labeled oligo DNAs were bound to streptavidin. Streptavidin, 100 μg, (Molecular Probes, Cat. No. S-2669) was dissolved in 10 μl of PBS. To this was added D2FB ($10^{-4}$ M) or A2FB ($10^{-4}$ M) dissolved in DEPC-water to give a streptavidin/oligo DNA molar ratio of 4:1, and the mixtures were allowed to stand at room temperature for 10 min. The D2FB/streptavidin solution was then mixed with the A2FB/streptavidin solution.

Figure 2C:
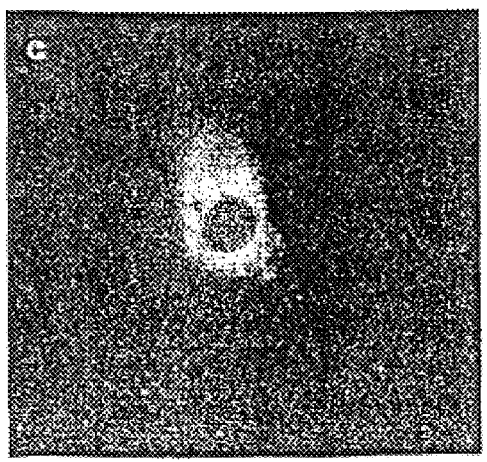
Figure 2D:
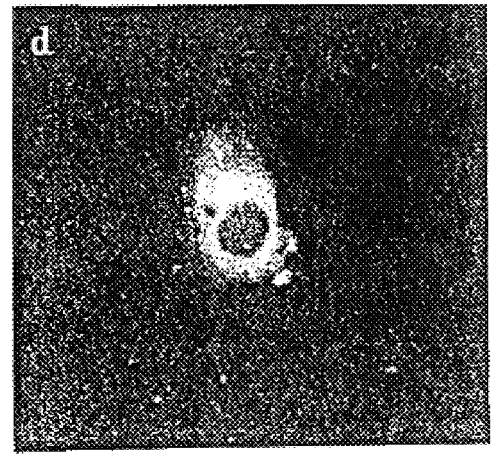

The streptavidin-bound fluorescently labeled oligo DNA solution was injected into Cos7 cells. Observation of the Bodipy493/503 fluorescence image and Cy5 fluorescence image of the cells revealed localization of both the D2FB/streptavidin probe and the A2FB/streptavidin probe in the cytoplasm (FIG. 2C, 2D). No change in distribution of the probes occurred after incubating the injected cells for one hour on the microscope stage. These results demonstrated that the streptavidin-bound oligo DNA probes localize in the cytoplasm and do not move to the nucleus. Furthermore, if the oligo DNA is digested by nucleases present in the cell, less than 20mer fluorescently labeled oligo DNA fragment is released from the streptavidin. The released oligo DNAs would rapidly move to and accumulate in the nucleus. Thus, the fact that the fluorescence intensity of the nucleus remains almost unchanged during one hour after injection indicates that little digestion of the streptavidin-bound oligo DNAs has occurred.

Figure 3:
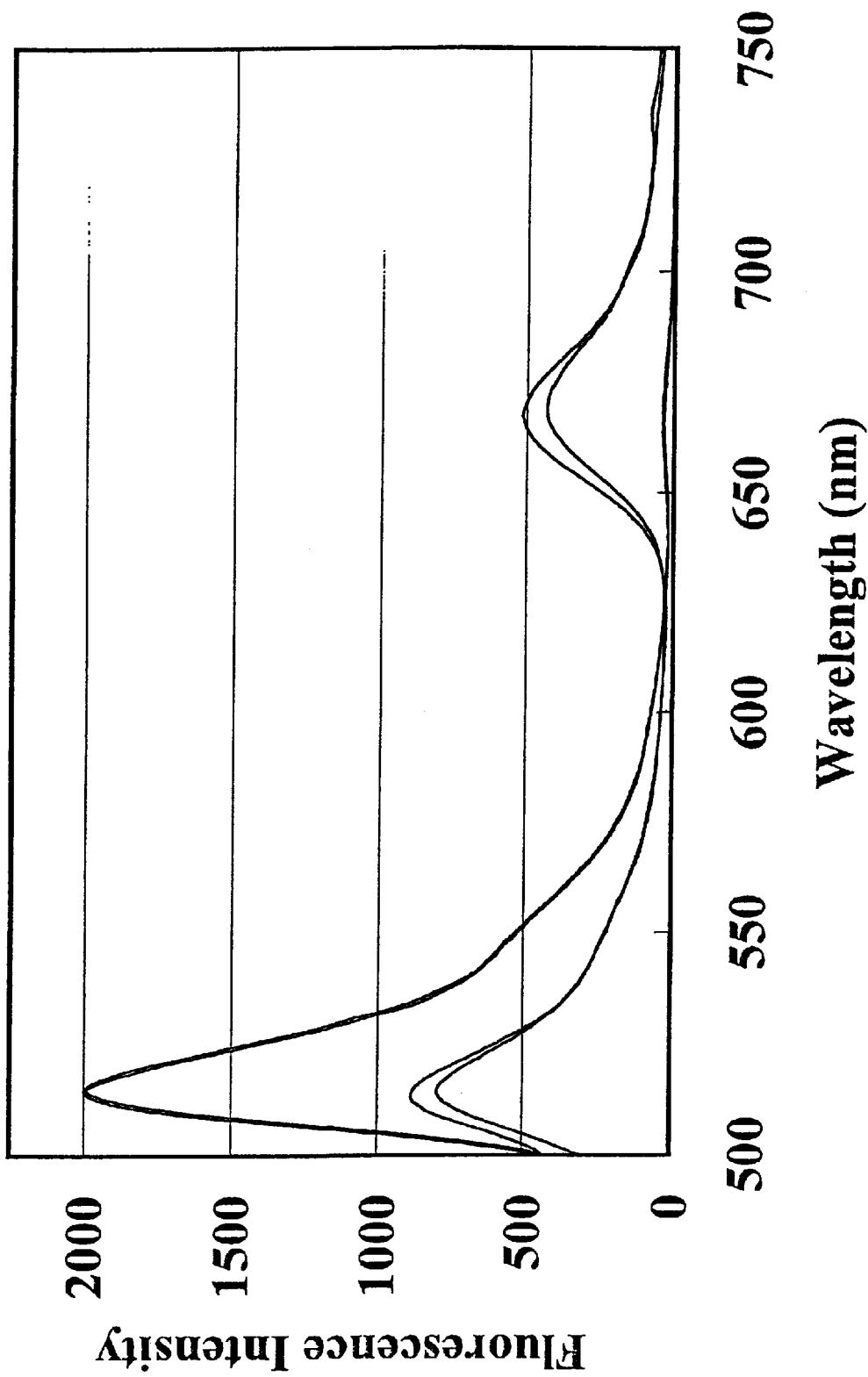
FIG. 3 is a graph showing change in the fluorescence spectrum when c-fos RNA was added to the solutions of two pairs of fluorescently labeled probes. In the figure, "a" represents the spectrum obtained when D2F and A2F were mixed at a molar ratio of 1:1; "b" represents the spectrum obtained when c-fos RNA synthesized by in vitro transcription reactions was added to the mixed solution of D2F/A2F and incubated for 15 minutes (D2F:A2F:c-fos RNA=1:1:1 (molar ratio)); "c" represents the spectrum obtained when D2FB/streptavidin and A2FB/streptavidin were mixed at a molar ratio of 1:1; and "d" represents the spectrum obtained when c-fos RNA was added to the mixed solution of D2FB/streptavidin and A2FB/streptavidin and incubated for 15 minutes (D2FB/streptavidin:A2FB/streptavidin:c-fosRNA=1:1:1 (molar ratio)).

The effect of streptavidin on hybridization of the fluorescently labeled probes to c-fos RNA was then investigated. Each $1\times10^{-6}$ M of streptavidin-bound fluorescently labeled probes (D2FB/streptavidin, A2FB/streptavidin) was mixed with $1\times10^{-6}$ M of c-fos RNA synthesized by in vitro transcription reactions in 1×SSC solution (molar ratio of 1:1) and the mixture was allowed to stand at room temperature for 15 min; and then the fluorescent spectra were measured. The same measurement was made using the fluorescently labeled probes (D2F, A2F) not bound to streptavidin, as a control experiment (FIG. 3). In all of the samples, addition of c-fos RNA decreased the Bodipy493/503 fluorescence intensity and increased the Cy5 fluorescence intensity. The degree of change was slightly lower with the streptavidin-bound fluorescently labeled probes. This suggests a small degree of steric hindrance by streptavidin on hybrid formation of the probes with c-fos RNA.

3. Preparation of c-fos mRNA-expressing Cells pSPT-cFos was treated with restriction enzyme EcoRI to cut out c-fos DNA (2.1 kb), and this was inserted into the EcoRI site of a pME18S expression vector (pME18S-cFos). The resulting expression vector (pME18S-cFos) was introduced into Cos7 cells by electroporation. The Cos7 cells were cultured in DMEM medium containing 10% fetal bovine serum, under conditions of 5% $CO_2$, 37° C. The Cos7 cells were removed off with a cell cleaver and washed with PBS, and then 5 $\mu$g of pME18S-cFos was added to the cell suspension ($1 \times 10^7$ cells/ml) on which a 930 V pulse voltage (BioRad: Gene Pulser II) was then applied. The resulting cell suspension was diluted 20-fold with DMEM medium and washed twice by centrifugation. The cells were suspended and plated to a glass-bottom dish (p35-0-14-C, MatTek, Ashland) for culturing.

4. Confirmation of Expression of c-fos mRNA 4-1. Dot blotting

Expression of c-fos mRNA in the Cos7 cells treated with the expression vector was confirmed by dot blotting. The cells were removed off by trypsin treatment after one day of plating, and washed with PBS. A QuickPrep Total RNA Extraction Kit (Pharmacia Biotech) was then used to extract the total RNA from the cells. The RNA solution extracted from the cells was transferred onto a nylon membrane and crosslinked thereto by ultraviolet irradiation (BioRad: Gene Linker). This was allowed to react with a digoxigenin (DIG)-labeled c-fos RNA probe (2.1 kb RNA with a sequence complementary to c-fos mRNA). Then, after reacting with alkali phosphatase-conjugated anti-DIG antibody, a DIG Nucleic Acid Detection Kit (Boehringer Mannheim) was used to form 4-nitroblue tetrazolium which was catalyzed by alkalinephosphatase. The quantity of the c-fos RNA probes hybridizing to the nylon membrane was determined by quantifying the amount of the formed 4-nitroblue tetrazolium using a densitometer. c-fos RNA of known concentrations that was synthesized by in vitro transcription reactions was plotted in like manner, and on that basis the quantity of the c-fos mRNA contained in the RNA fractions that had been extracted from the cells was estimated. The DIG-labeled c-fos RNA probes were prepared by in vitro transcription reactions, in which a linearized pBluescript-cFos prepared by treatment of the plasmid with the restriction enzyme EcoRV was used as a target and T3 RNA polymerase was driven. The reactions were performed using a T7 MEGAscript kit (Ambion). The expression of c-fos mRNA was confirmed at 12, 24, 48, 72 and 96 h after transfection.

4-2. in situ hybridization

Fluorescence in situ hybridization (FISH) was performed to confirm the ratio of expressing cells. The FISH was carried out according to a known protocol. After Cos7 cells treated with pME18S-cFos were cultured for one day, the cells were fixed for 15 min at room temperature with 4% paraformaldehyde/PBS (pH 7.4). The fixed cells were treated with the DIG-labeled c-fos RNA probe. The cells were then stained with the FITC-conjugated anti-DIG antibody and observed under a fluorescence microscope. It was confirmed that more than 80–90% of the transfected cells expressed c-fos mRNA.

5. Confirmation of Hybridization of Probes to c-fos mRNA in Living Cells by in situ Transcription The following experiment was conducted to confirm that the fluorescently labeled probes (D2F, A2F) hybridize to c-fos mRNA in the c-fos mRNA-expressing cells when introduced therein. Specifically, the probes were introduced into the cells when they were alive, and the cells were then fixed. Reverse transcription was carried out using the introduced probes as primers in the fixed cells, and synthesis of cDNA was detected (in situ transcription method (IST method), Politz, J. C., Taneja, K. L., Singer, R. H. (1995), Nucleic Acids Research, 23, 4946–4953). Cos7 cells transfected with pME18S-cFos were cultured overnight. The fluorescently labeled probes and the transfection reagent TransFast (Promega) were mixed at a charge ratio of 1:1. The mixture, 10 $\mu$M (final concentration), was added to the cells which were pre-cultured in serum-free medium for one hour, and the cells were incubated at 37° C. for one hour. After washing the cells, they were treated with 4% paraformaldehyde/PBS (pH 7.4) at room temperature for 15 min to fix the cells. The cell membrane permeability was increased by treatment with 0.5% TritonX-100 (90 sec), and then the cells were immersed in a transcription reaction solution containing Moloney Murine Leukemia Virus Reverse Transcriptase (RNaseH-), 0.35 mM DIG-labeled dUTP and 1 mM dNTP and incubated at 30° C. for 1.5 h for reverse transcription reactions. The cells were then treated with the FITC-conjugated anti-DIG antibody and observed with a fluorescence microscope.

As a result, the transfected cells into which D2F had been introduced exhibited strong fluorescence in the whole cytoplasm. That is, c-fos cDNA had been synthesized in the cytoplasm. When D2F was introduced into Cos7 cells that had not been transfected, no fluorescence was observed in the cytoplasm. No fluorescence was observed in the cells when an oligo DNA with the same sequence as the 657–676 site of c-fos mRNA (sense probe, with a base sequence complementary to D2F) was allowed to act on the transfected cells. These results confirmed that D2F hybridizes to c-fos mRNA in living Cos7 cells that express c-fos mRNA due to transfection. Similar results were obtained for A2F, confirming that A2F also hybridizes to c-fos mRNA in Cos7 cells.

The base sequences of the sense probes used in the experiment were the following. The synthesis and purification were carried out by the method described above.

Oligo DNA with sequence of 657–676 site

5'-(Bodipy493/503)GCGGAGACAGACCAACTAGA-3'

Oligo DNA with sequence of 677–696 site

5'-AGATGAGAAGTCTGCT(Cy5)TTGC-3'

6. Change in Fluorescence Image Resulting from Hybrid Formation in Living Cells

A solution of D2FB/streptavidin as the donor probe and A2FB/streptavidin as the acceptor probe mixed in a molar ratio of 1:1 (probe concentration: $2 \times 10^{-5}$ M, PBS buffer) was injected into Cos7 cells. A fluorescence microscope was used to take DD images (Bodipy493/503 fluorescence) and AA images (Cy5 fluorescence), as well as DA images (image of the Cy5 fluorescence by irradiation of light with the excitation wavelength of Bodipy493/503), in order to observe the FRET from Bodipy493/503 to Cy5. The DA images were observed using the following filters:

Excitation filter: BP450–490
Dichroic mirror: FT510
Barrier filter: BP660–710

When FRET occurs, the fluorescence intensity of the DD image (donor) decreases while the fluorescence intensity of the DA image (acceptor) increases. The ratio of the fluorescence intensities of the DA image and DD image (DA/DD) represents the efficiency of FRET. This was confirmed by the following experimental results. Here, when the ratio of the DA and DD images was to be obtained, processing was performed to subtract background from the respective images.

Figure 4:
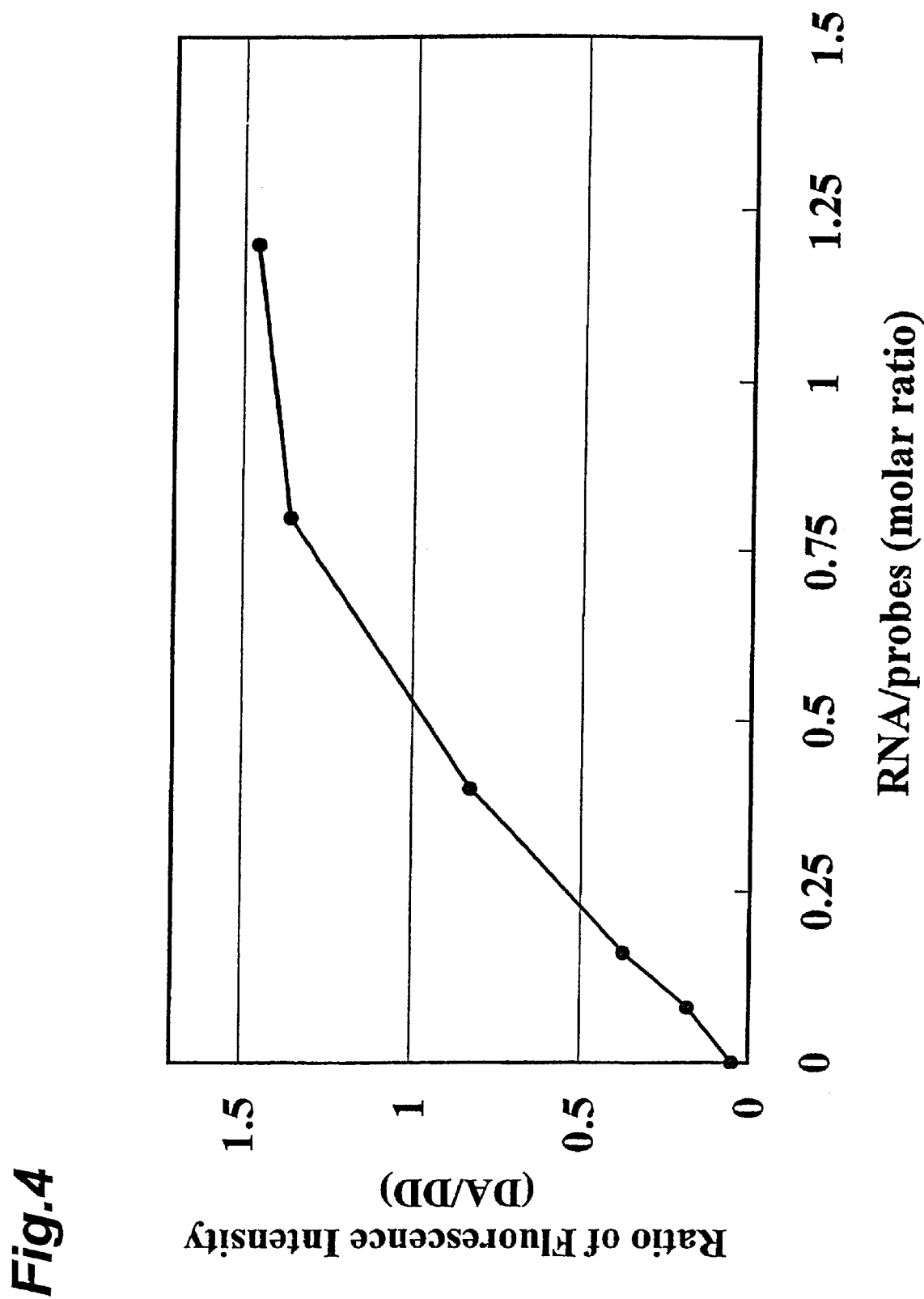
FIG. 4 is a graph showing change in the fluorescence intensity ratio (DA/DD) in fluorescence microscope images (DD images and DA images) with formation of a 3-member hybrid of the probe pair and target RNA. In the figure, a 40 mer RNA with a base sequence complementary to the probes was mixed at different ratios with a pair of the D2FB/ streptavidin and A2FB/streptavidin solutions (molar ratio of D2FB/streptavidin and A2FB/streptavidin=1:1), and the mixtures were incubated at room temperature for 15 minutes. The DD images and DA images were taken from the incubated solutions under a fluorescence microscope, and the ratios of the DD values and DA values (DA/DD) were plotted against the ratios of RNA to probes (RNA/probes).
Figure 5A:
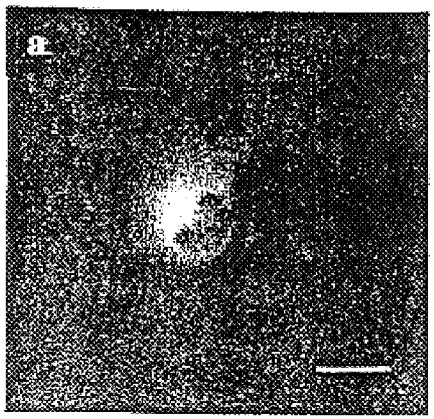
FIGS. 5A–5D are a set of fluorescence micrographs showing change in the fluorescence images of a cell into which a pair of fluorescently labeled probes had been introduced, after a target RNA was introduced by injection into the cell. A solution of D2FB/streptavidin and A2FB/streptavidin mixed at a molar ratio of 1:1 was introduced into Cos7 cells by microinjection.
Figure 5B:
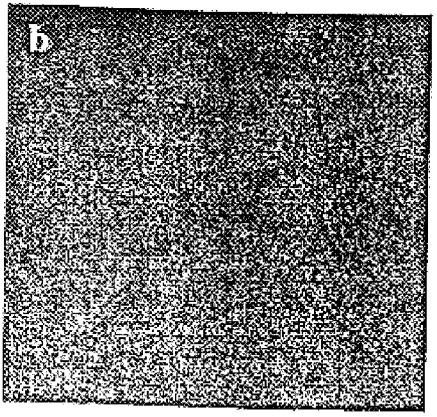
Figure 5C:
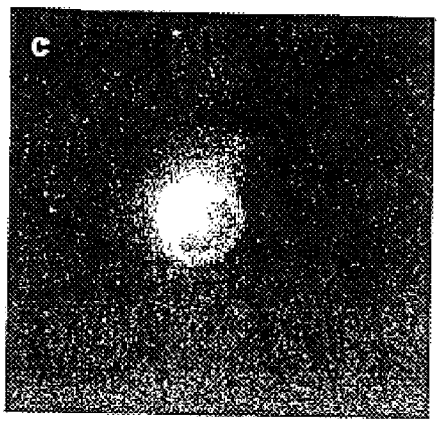
Figure 5C:
Figure 5D:
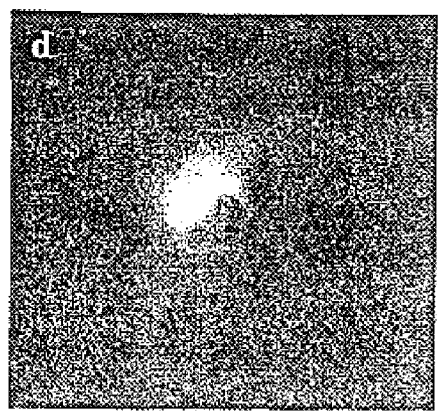
Figure 6A:
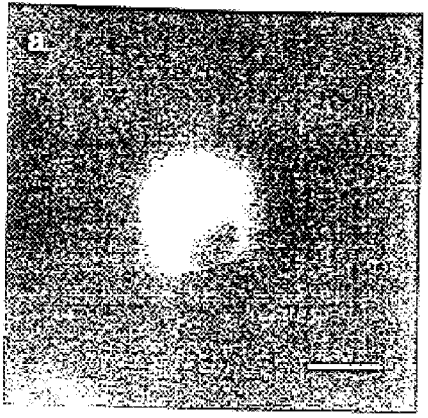
FIGS. 6A–6D are a set of fluorescence micrographs showing change in the fluorescence images of a cell into which a pair of fluorescently labeled probes had been introduced, after a non-target DNA was introduced by injection into the cell. A solution of D2FB/streptavidin and A2FB/streptavidin mixed at a molar ratio of 1:1 was introduced into Cos7 cells by microinjection.
Figure 6C:
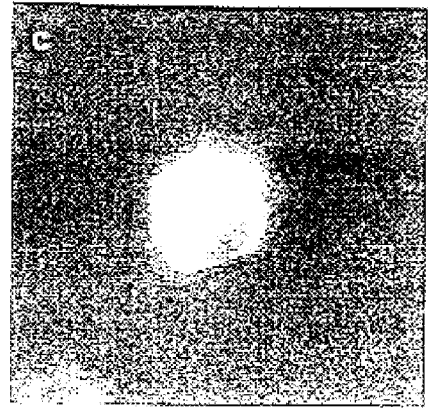
Figure 6B:
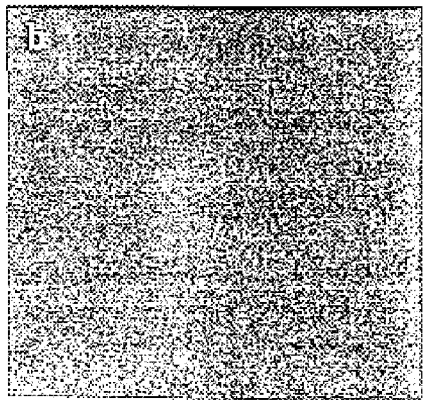
Figure 6D:
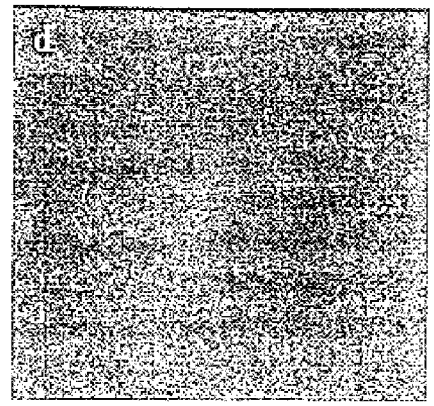

Specifically, D2FB/streptavidin and A2FB/streptavidin were mixed in 1×SSC solution at 1×10$^{-5}$ M each (molar ratio of 1:1). To this was added a 40 mer RNA with a base sequence complementary to the probes at ratios of 0.1, 0.2, 0.5, 0.75, 1.0 and 1.25, and the mixtures were allowed to stand at room temperature for 30 min. Each donor probe/acceptor probe/40 mer RNA mixture was then dropped onto a cover slip and the fluorescence images (DD image, DA image) of each solution were taken. The ratio of the fluorescence intensity of the DD image and the fluorescence intensity of the DA image (DA/DD) was obtained, and was plotted against the molar ratio of the RNA and probes (RNA/probes) (FIG. 4).

Larger amount of the 40 mer RNA was added, a decrease of fluorescence intensity in the DD image and an increase of fluorescence intensity in the DA image became larger. That is, the DA/DD value increases in response to increasing the amounts of hybrid formed among D2FB/streptavidin, A2FB/streptavidin and the 40 mer RNA. The DA/DD value increased from 0.08 for the probes alone (RNA/probes=0) to 1.5 for RNA/probes=1.

Figure 7:
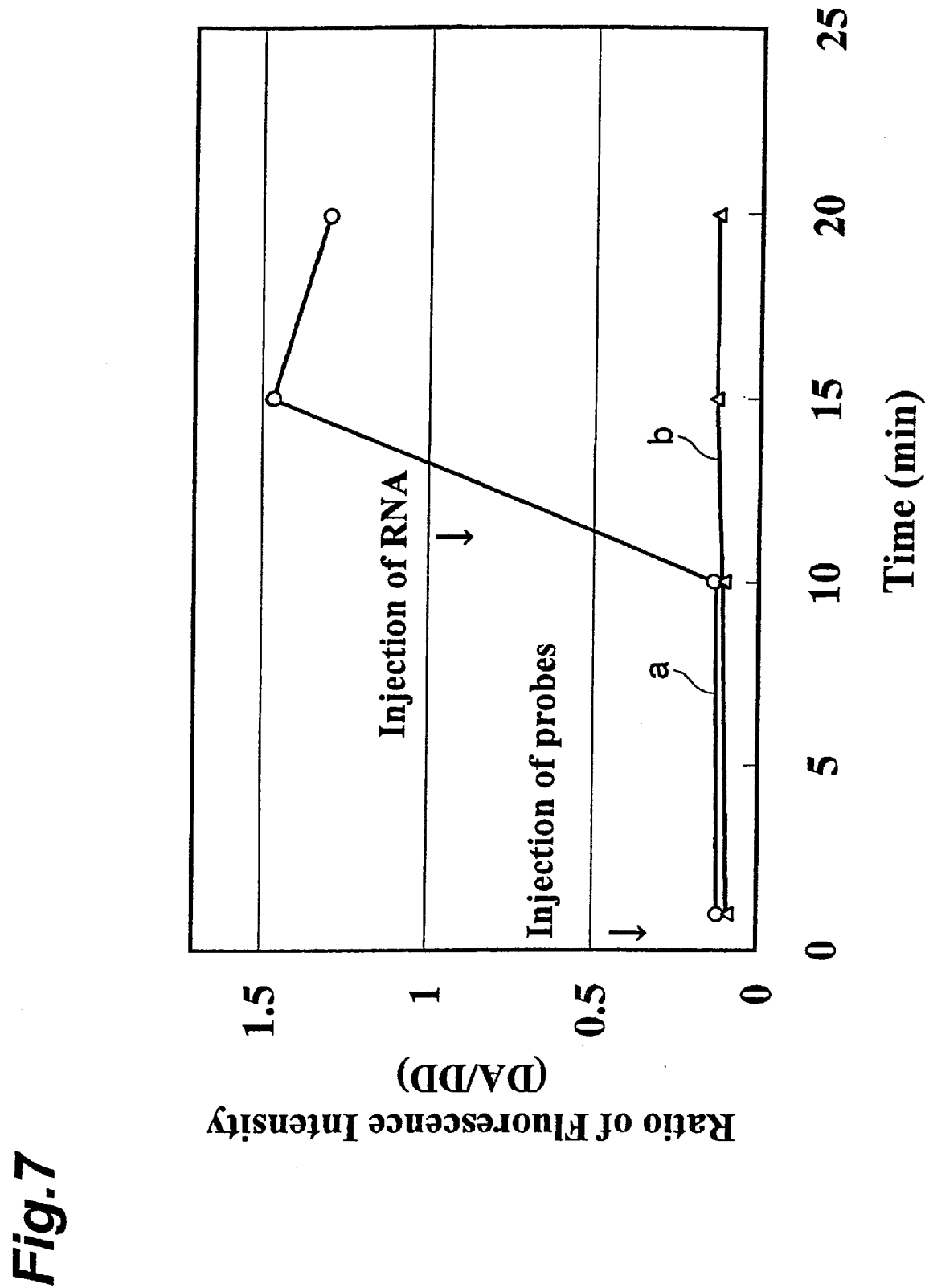
FIG. 7 is a graph showing the changes in DA/DD values in the cytoplasm plotted against time for the experiment of FIGS. 5A–5D and 6A–6D. In the figure, "a" represents the cell of FIGS. 5A–5D, and "b" represents the cell of FIGS. 6A–6D.
Figure 8A:
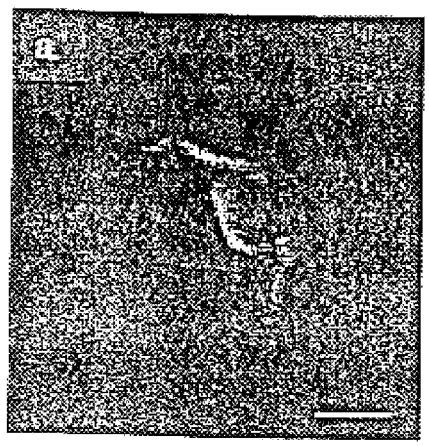
FIGS. 8A–8D are a set of fluorescence micrographs showing the time-dependent change in the fluorescence images of a mRNA-expressing cell after introduction of a pair of fluorescently labeled probes by microinjection. Here, the streptavidin-bound probes with no linker (D2FB, A2FB) were introduced into transfected a Cos7 cell.
Figure 8B:
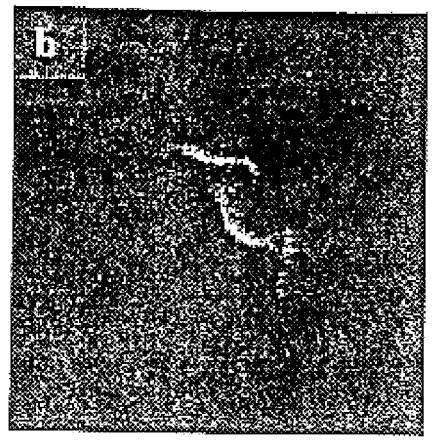
Figure 8C:
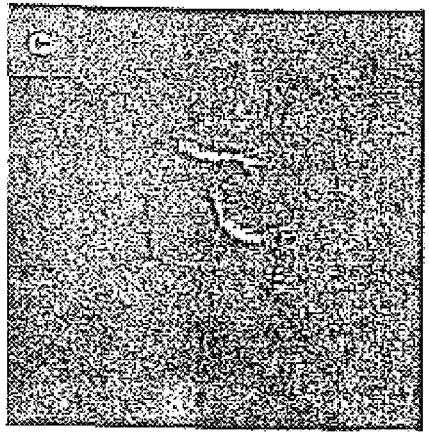
Figure 8D:
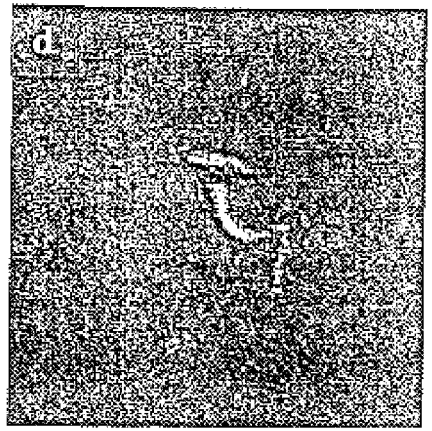
Figure 9A:
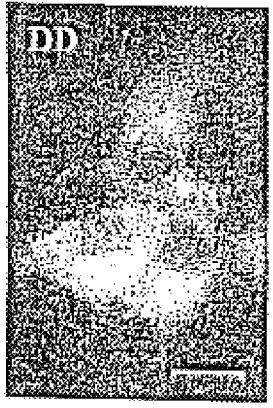
FIGS. 9A–9D are a set of fluorescence micrographs showing fluorescence images of an mRNA-expressing cell after introduction of a pair of fluorescently labeled probes by microinjection. Here, the streptavidin-bound linker-introduced probes (D2FBL, A2FBL) were introduced into a transfected Cos7 cell.
Figure 9B:
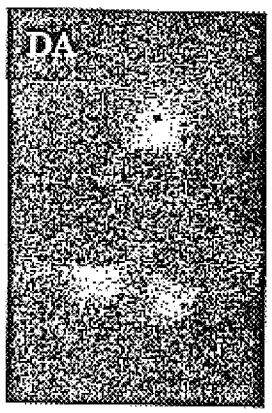
Figure 9C:
Figure 9D:

The DA/DD value was 0.08 in the cytoplasm of the Cos7 cells immediately after injection of the D2FB/streptavidin and A2FB/streptavidin mixture, and this value was the same as the value for the injection solution. No change was observed in the DA/DD value after incubating the cells on the microscope stage for 15 min. The cells were then injected with a 40 mer RNA (2×10$^{-5}$ M, dissolved in DEPC-water) that had the same sequence as the 657–696 site of c-fos mRNA. The fluorescence image taken after 2 min showed a decrease in fluorescence intensity in the cytoplasm in the DD image and an increase in fluorescence intensity in the DA image (FIGS. 5A–5D). The DA/DD value was 1.5. The DA/DD values plotted against time are shown in FIG. 7.

By referring to FIGS. 5A–5D, it is understood that most of the donor probes and the acceptor probes in the cytoplasm formed 3-member hybrids with the 40 mer RNA. When a 40 mer DNA with the antisense sequence to the 657–696 site of c-fos mRNA (prepared by linking the donor probe base sequence with the acceptor probe base sequence continuously) was injected as a control experiment, no change was observed in the fluorescence images (FIGS. 6A–6D). These results indicate that both D2FB/streptavidin and A2FB/streptavidin introduced into the cytoplasm can rapidly hybridize to the target RNA when it is present (i.e., the probes can freely diffuse in the cytoplasm) and that the fluorescence images change and, as the result, the DA/DD value increases with formation of a 3-member hybrid of the donor probe, acceptor probe and target RNA in the cytoplasm.

The base sequences of the RNA and DNA used in the experiment were the following, and the synthesis and purification were carried out by the method described above.

40 mer RNA with same sequence as 657–696 site of c-fos mRNA
5'-GCGGAGACAGACCAACUAGAAGAUGAGAAGUCUGCUUUGC-3'

40 mer DNA with same sequence as 657–696 site of c-fos mRNA
5'-GCGGAGACAGACCAACTAGAAGATGAGAAGTCTGCTTTGC-3'

40 mer DNA with antisense sequence to 657–696 site of c-fos mRNA
5'-GCAAAGCAGACTTCTCATCTTCTAGTTGGTCTGTCTCCGC-3'

7. Detection of c-fos mRNA in Living Cells

A solution of mixtures of D2FB/streptavidin as the donor probe and A2FB/streptavidin as the acceptor probe mixed at a molar ratio of 1:1 (probe concentration: 2×10$^{-5}$ M, PBS buffer) was injected into Cos7 cells that had been transfected with pME18S-cFos (cells expressing c-fos mRNA).

No increase in the DA/DD value in the cytoplasm was observed during 20 min after injection (FIGS. 8A–8D and FIG. 12). This result suggests that streptavidin produces steric hindrance to hybridization of the oligo DNA probes to the c-fos mRNA in the cytoplasm. Thus, an oligo DNA having a "linker" introduced between the oligo DNA for hybridization and streptavidin was used as a probe. Oligo DNA was used as the "linker"; 10 C (cytosine) was attached to the 3'-end of the donor probe, and 20 C was attached to the 5'-end of the acceptor probe.

The streptavidin-bound oligo DNA probes used in the experiment were the following, and the synthesis and purification of the oligo DNAs, and binding with streptavidin, were carried out in the manner described above.

Linker-introduced donor probe (D2FBL):
5'-(Bodipy493/503)TCTAGTTGGTCTGTCTCCGCCCCCCCCCC(Biotin)-3'-(streptavidin)

Linker-introduced acceptor probe (A2FBL):
(streptavidin)-5'-(Biotin)CCCCCCCCCCCCCCCCCCCCGCAAAGCAGACTTCTC(Cy5)ATCT-3'

Figure 10A:
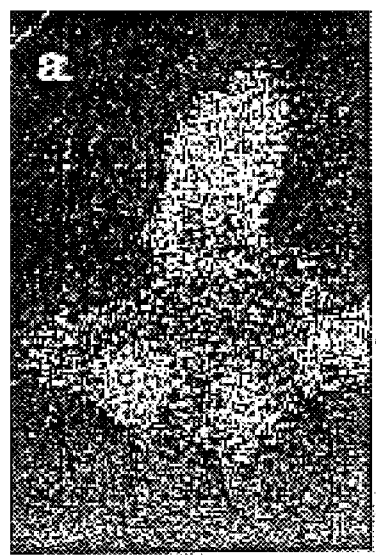
FIGS. 10A and 10B are pseudocolor representations of the ratio image obtained by dividing the DA image by the DD image in the experiment of FIGS. 9A–9D.
Figure 10B:
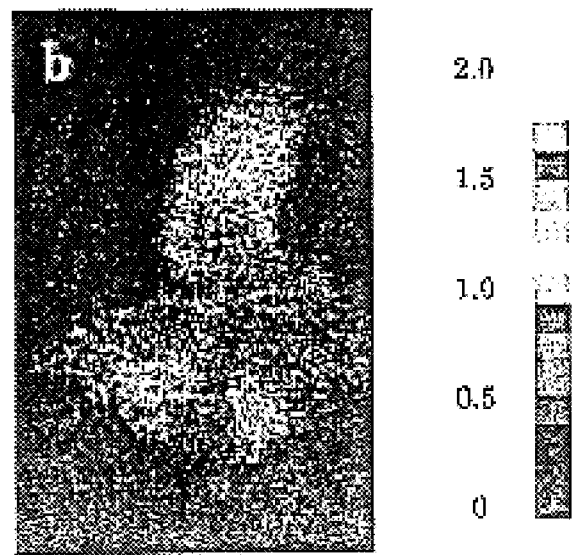
Figure 11A:
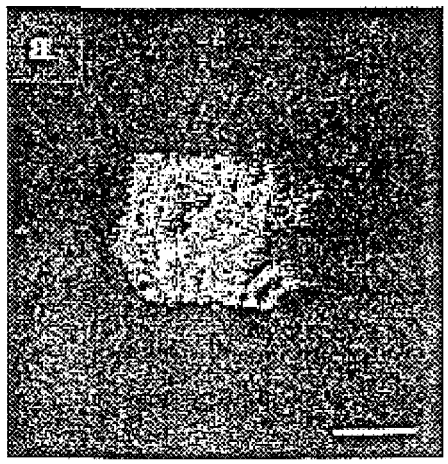
FIGS. 11A–11D are a set of fluorescence micrographs showing the time-dependent change in the fluorescence images of an mRNA-expressing cell after introduction of a pair of fluorescently labeled probes by microinjection. Here, D2FBL and A2FBL were introduced into a transfected Cos7 cell.
Figure 11B:
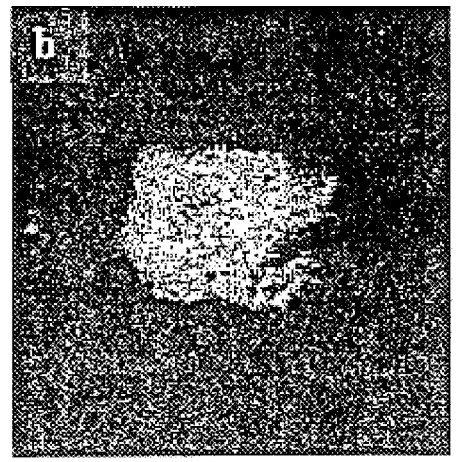
Figure 11C:
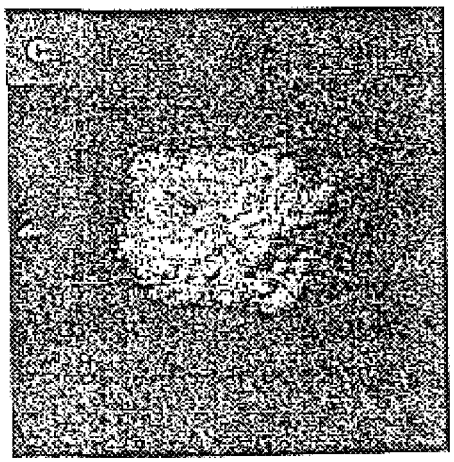
Figure 11D:
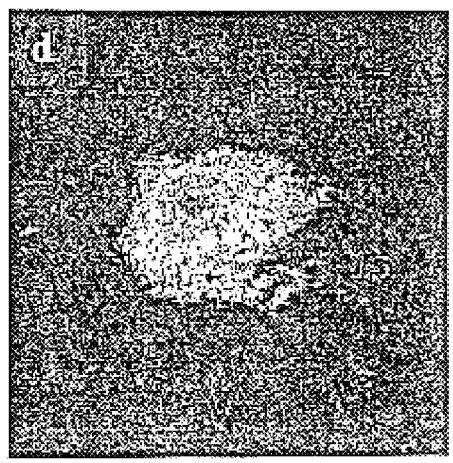
Figure 12:
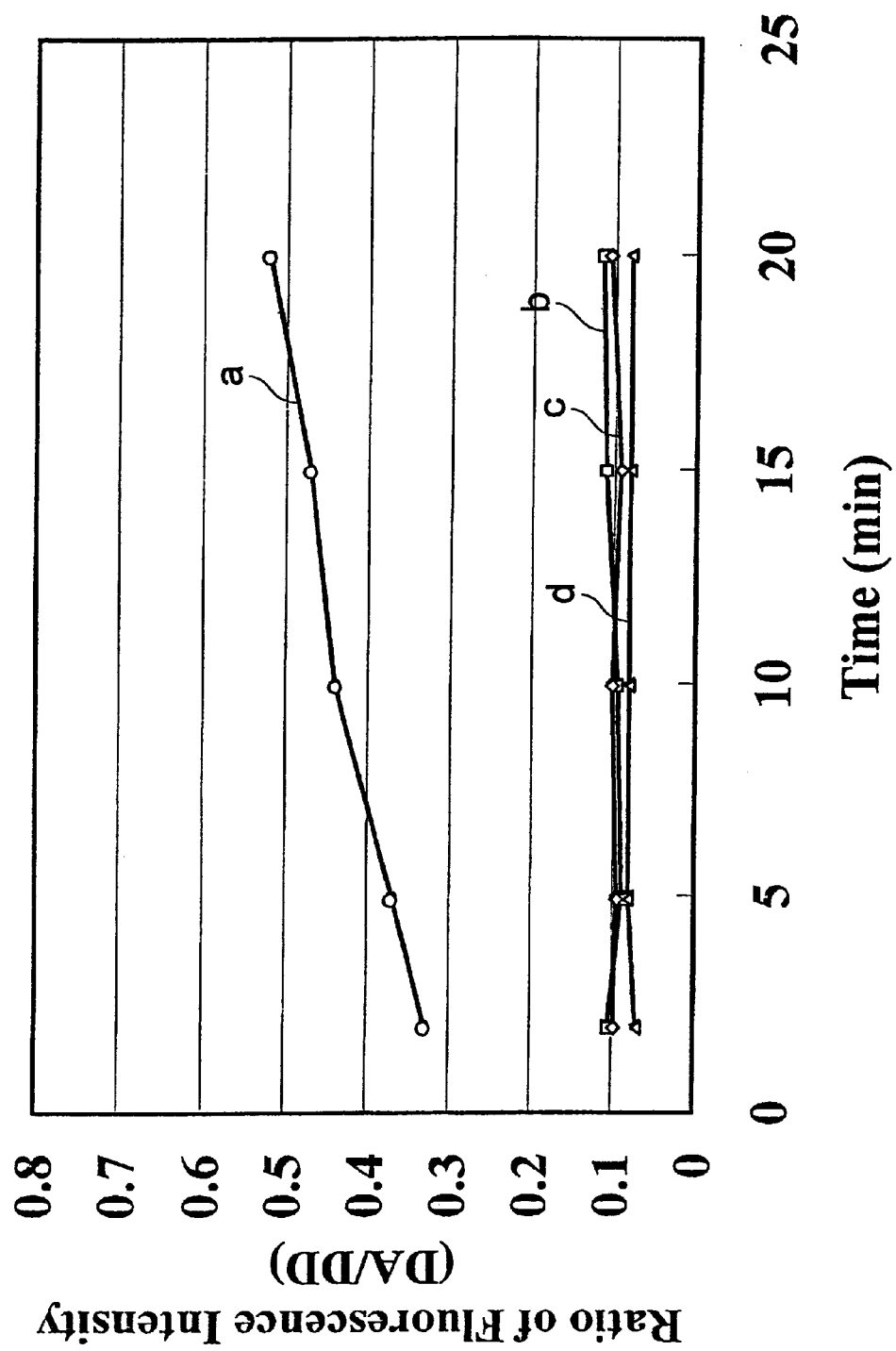
FIG. 12 is a graph showing DA/DD values for the cytoplasm of the cells used in the experiments of FIGS. 8A–8D, 11A–11D, 13A–13D and 14A–14D plotted against time. In the figure, "a" represents the cell of FIG. 11A–11D, "b" the cell of FIG. 13A–13D, "c" the cell of FIG. 14A–14D and "d" the cell of FIG. 8A–8D.
Figure 13A:
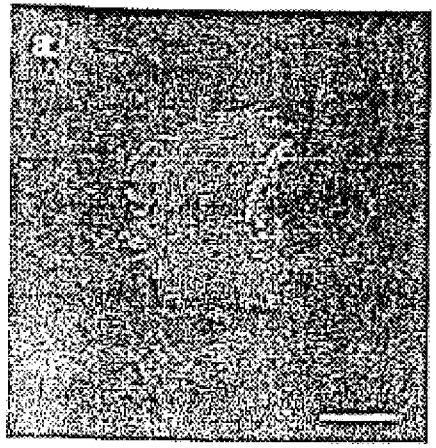
FIGS. 13A–13D are a set of fluorescence micrographs showing the time-dependant change in fluorescence images of an mRNA-expressing cell after introduction of a pair of fluorescently labeled probes by microinjection. Here, D2FBL and A2FBL were introduced into a non-transfected Cos7 cell.
Figure 13B:
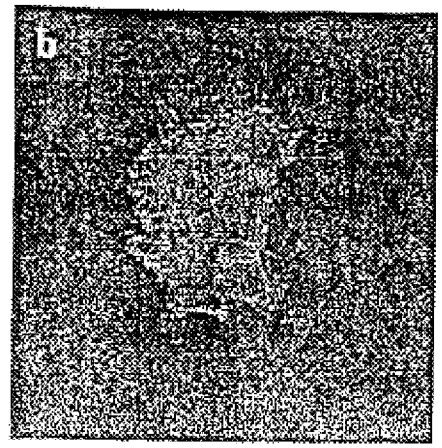
Figure 13C:
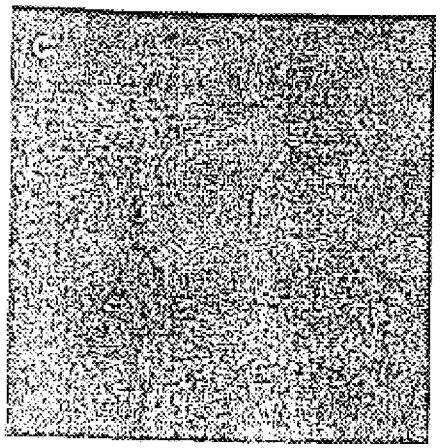
Figure 13D:
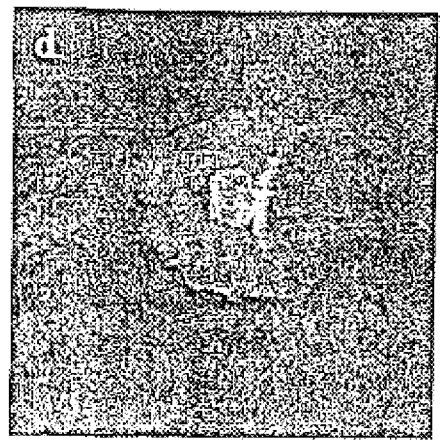
Figure 14A:
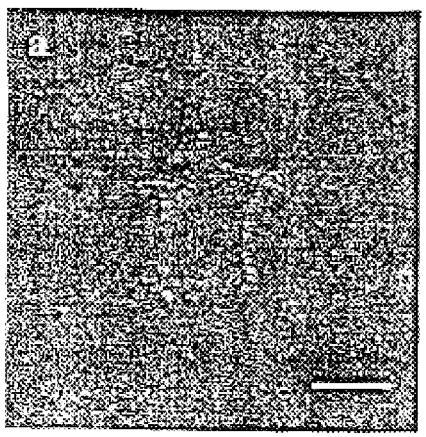
FIGS. 14A–14D are a set of fluorescence micrographs showing the time-dependant change in fluorescence images of an mRNA-expressing cell after introduction of a pair of fluorescently labeled probes by microinjection. Here, the streptavidin-bound linker-introduced probes (D2SFBL and A2SFBL: sense sequence probes) were introduced into a transfected Cos7 cell.
Figure 14B:
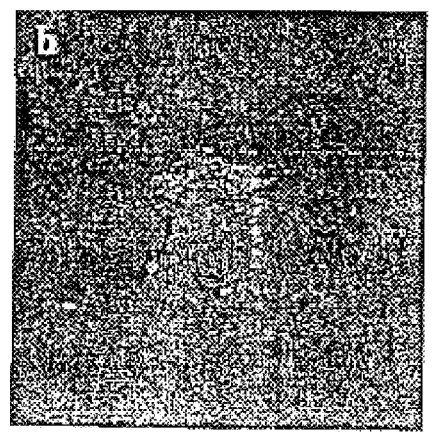
Figure 14C:
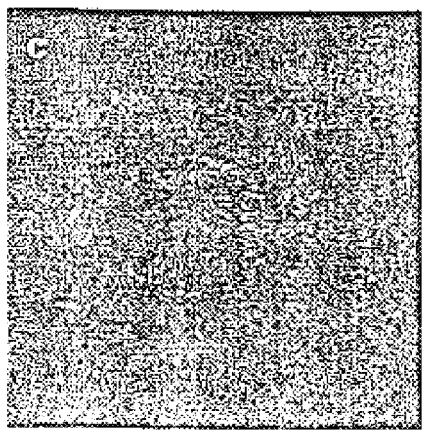
Figure 14D:
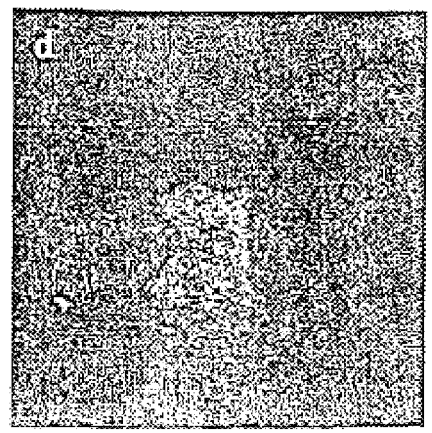
Figures 15A, 15B, 15C, 15D:
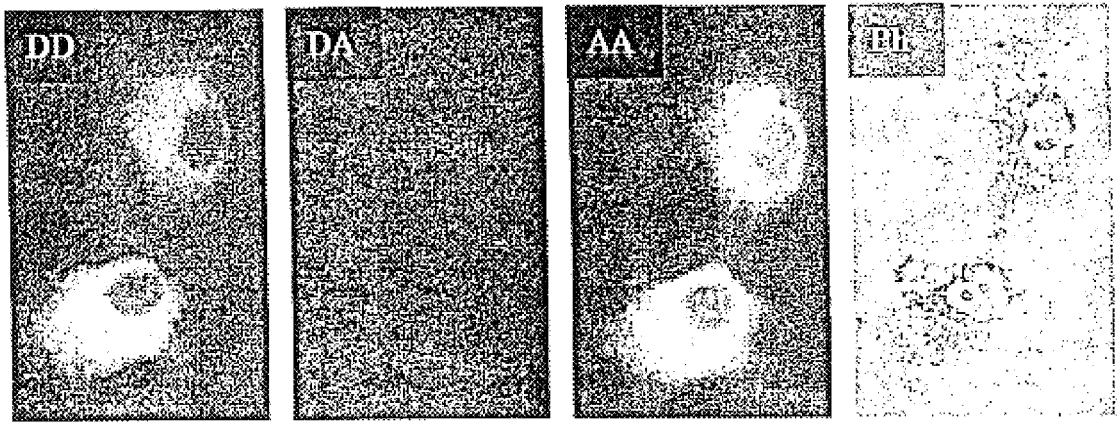
FIGS. 15A–15D are a set of fluorescence micrographs showing fluorescence images of an mRNA-expressing cell after introduction of a pair of fluorescently labeled probes by microinjection. Here, D2SFBL and A2SFBL were introduced into a transfected Cos7 cell.

D2FBL and A2FBL were mixed in a molar ratio of 1:1, and were injected into Cos7 cells transfected with pME18S-cFos (Cos cells expressing c-fos mRNA). FIGS. 9A through 9D show the DD image, DA image, AA image and phase contrast (Ph) image taken 5 min after injection, respectively. The AA image shows that Cy5 fluorescence was observed throughout the whole cytoplasm, and the strong fluorescence was observed in a certain region near the nucleus. This indicates that while Cy5 (i.e., the acceptor probe A2FBL) is diffusely distributed throughout the whole cytoplasm, its concentration is higher in the certain regions near the nucleus. The DD image shows that Bodipy493/503 fluorescence was observed throughout the whole cytoplasm. Relatively strong Bodipy 493/503 fluorescence is also observed in the region near the nucleus similarly to the distribution of the C5 fluorescence, but not as clearly as in the AA image. The DA image presenting fluorescence due to FRET shows that quite strong fluorescence was observed in the same regions where strong fluorescence was observed in the DD image and AA image. These fluorescence images indicate that the donor probes and acceptor probes are present at higher concentrations in regions near the nucleus, and that FRET occurs with higher efficiency in these regions than in the other regions of the cytoplasm. FIG. 10A shows the DA/DD ratio image at 5 min after injection, which evaluates the FRET efficiency in the cells and is presented in pseudo-color. According to FIG. 10A, the DA/DD values were non-uniformly distributed throughout the cell. The DA/DD values in the regions near the nucleus were 0.7–1.2, and 0.3–0.4 in the other regions. These values were larger than the value for the injection solution (0.08), indicating that FRET had occurred in most of the cytoplasm. FIG. 10B shows the DA/DD ratio image at 20 min after injection in pseudo-color. The distribution pattern of fluorescence remains almost unchanged from FIG. 10A; the DA/DD value increased. This indicates that hybridization of the probes to the c-fos mRNA had been progressing during 20 min after injection. FIGS. 11A through 11D are other examples of DA/DD images, and also exhibits changes in the fluorescence images with time. The DA/DD values increased in some regions of the cytoplasm 5 min after injection. Further, increasing DA/DD values were observed in the cytoplasm as time progressed. The DA/DD values in the nucleus, however, were still low values. FIG. 12 is a graph showing the average DA/DD values in the cytoplasm plotted against time after injection.

When the same pair of probes was injected into Cos7 cells that had not been transfected with pME18S-cFos (c-fos mRNA non-expressing cells) as a control experiment, the DA/DD values were approximately as low as the value for the injection solution (0.08) (FIG. 12, FIGS. 13A–13D). When a mixture of the acceptor probe with the same base sequence as the 657–676 site of c-fos mRNA and the donor probe with the same base sequence as the 677–696 site thereof (probes with sense sequences, which probes contained the same linker portions as the antisense probes mentioned above) was injected into Cos7 cells transfected with pME18S-cFos (c-fos mRNA-expressing cells) as another control experiment, the DA/DD values were approximately as low as the value for the injection solution (0.08) (FIG. 12, FIGS. 14A–14D). FIGS. 15A through 15D shows the DD image, DA image, AA image and phase contrast image of a cell taken 5 min after injection, respectively. The DD image and AA image show that both Bodipy493/503 fluorescence and Cy5 fluorescence was observed uniformly throughout the whole cytoplasm. In the DA image, little fluorescence was observed. FIG. 16A, similarly to FIG. 10A, shows the DA/DD ratio image at 5 min after injection in pseudo-color. The DA/DD values are approximately 0.1, viz., approximately the same value for the injection solution (0.08). FIG. 16B shows the DA/DD ratio image of another cell at 20 min after injection in pseudo-color. From this image it is seen that the distribution of fluorescence and the DA/DD values were unchanged during 20 min after injection. These results indicate that no FRET occurred, and therefore that no hybrids were formed in these control samples.

The streptavidin-bound oligo DNA probes used in the experiment were the following, and the synthesis and purification of the oligo DNAs, and binding with streptavidin, were carried out by the method described above.
Linker-introduced sense probes
With same base sequence as 657–676 site (D2SFBL):
  5'-(Bodipy493/503)
    AGATGAGAAGTCTGCTTTGC-
    CCCCCCCCCCCCCCCCCCCC C(Biotin)-3'-
    (streptavidin)
With same base sequence as 677–696 site (A2SFBL)
  (streptavidin)-5'-(Biotin)
    CCCCCCCCCCGCGGAGACAGACCAAC (Cy5)
    TAGA-3'

The above results indicate that hybridization with c-fos mRNA by the donor probe having the base sequence complementary to the 657–676 site of c-fos mRNA and the acceptor probe having the base sequence complementary to the 677–696 site of c-fos mRNA, which was introduced into the cells, was detectable as a fluorescence image under a microscope. The donor probe and acceptor probe with no linker portion form hybrids with c-fos RNA in vitro (in an aqueous solution). In cells, they also form hybrids with 40 mer RNA having the complementary base sequence. Notwithstanding, when these probes were introduced into c-fos mRNA-expressing cells, no FRET was observed in the cytoplasm (no increase in the DA/DD values occurred), which suggests that the degree of steric hindrance by streptavidin to hybridization of the probes with c-fos mRNA is much greater intracellularly than in aqueous solution.

Example 3

Estimation of the Quantity of c-fos mRNA Expression in Living Cells

Figure 17:
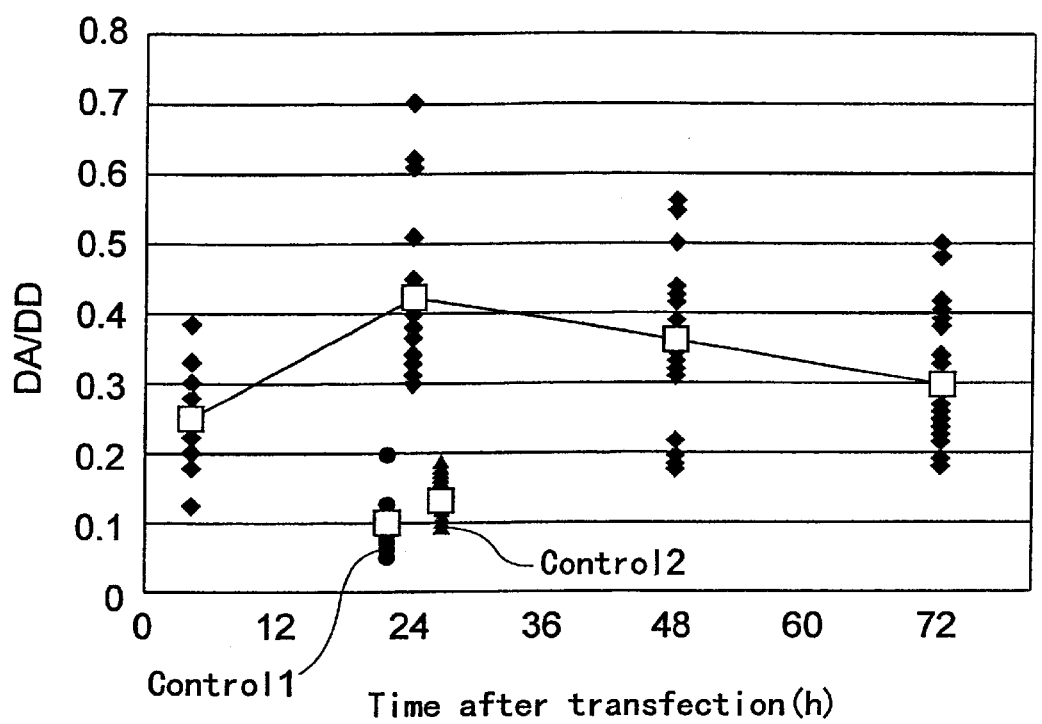
FIG. 17 is a graph showing DA/DD values for the cytoplasm in the individual cells injected with probes. Here, a solution of D2FBL and A2FBL mixed at $1\times10^5$ molecules each was introduced into transfected Cos7 cells by microinjection at 3–5, 24, 48 and 72 hours after transfection. As a control, D2FBL and A2FBL were injected into non-transfected cells (control 1) and D2SFBL and A2SFBL were injected into transfected cells (control 2). In the figure, the symbol "◆, ●, or ▲" each represents the DA/DD value for the individual cell, and the symbol "□" represents the average DA/DD value for the group of cells at a particular time.

In the same manner as Example 2, approximately $10^5$ molecules of the linker-introduced donor probe (D2FBL) and the linker-introduced acceptor probe (A2FBL) were injected into individual Cos7 cells that had been transfected with pME18S-cFos, at 3–5, 24, 48 and 72 hours after transfection. The total fluorescence intensity of the cytoplasm for the DD image and the DA image were determined respectively, and the DA/DD values for the individual cells were estimated. In FIG. 17, the DA/DD value for each cell was plotted. The average value among the cells at each time was also shown. The DA/DD values were larger than 0.1, and there was large divergence between cells. As a control experiment, the probes were injected into Cos7 cells that had not been transfected with pME18S-cFos, in the same manner as Example 2. As another control experiment, probes with the sense sequence (D2SFBL and A2SFBL) were injected into Cos7 cells that had been transfected with pME18S-cFos. The injection was carried out 24 h after transfection. The DA/DD values for the control samples were approximately 0.1, which was almost the same as the value for the injection solution (0.08).

Figure 18:
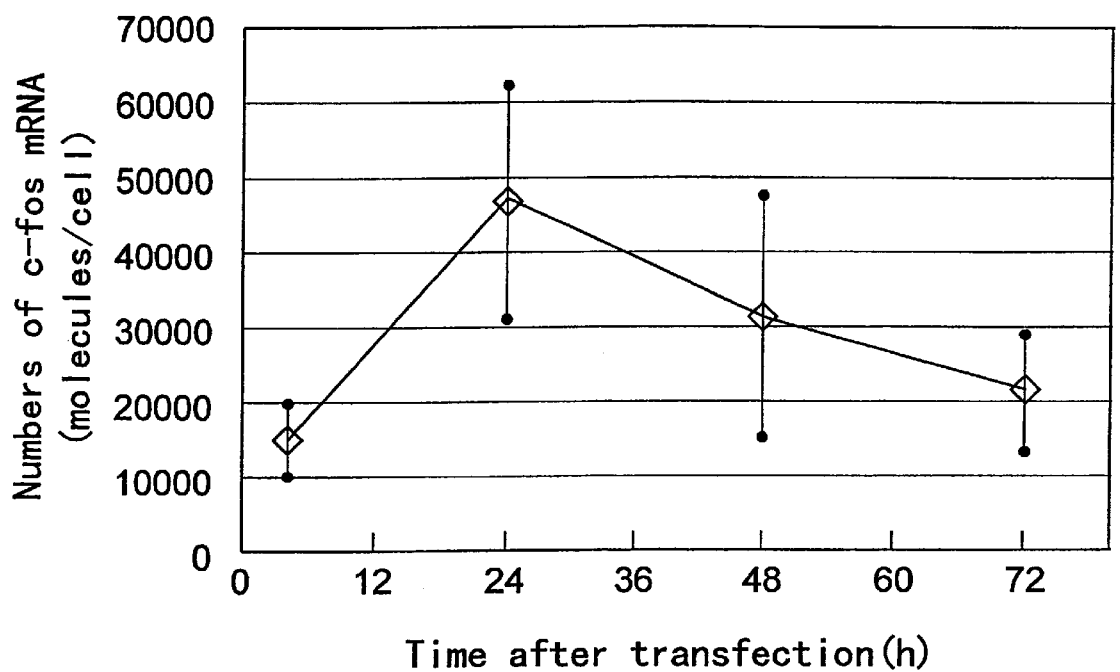
FIG. 18 is a graph showing the average number of molecules of c-fos mRNA expressed per cell after transfection, as the result of deduction by dot blotting, plotted against time.

The average number of hybrid present in the cytoplasm per cell was calculated from the average DA/DD value. Here, the total number of probe molecules in the cell was assumed to be $10^5$. As a result, values of approximately 13,000, 30,000, 24,000 and 19,000 were obtained for the injection experiments at 3–5, 24, 48 and 72 h after injection, respectively. These values approximately match the values determined by dot plotting the number of molecules of expressed c-fos mRNA per cell (FIG. 18). This method can therefore assay the expression of genes (mRNA) on the single cell level.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method for detecting a target nucleic acid existing in cytoplasm of a living cell, the method comprising:
   introducing into the cytoplasm, a detection probe bound to a nuclear membrane unpermeable molecule via a linker and labeled with a fluorescent dye, the probe having a base sequence capable of hybridizing to the target nucleic acid; forming a hybrid between the target nucleic acid and the probe; determining any change in fluorescence of the fluorescent dye due to formation of the hybrid; and
   thereby detecting the target nucleic acid existing in the cytoplasm of a living cell.

2. The method according to claim 1, wherein the detection probe is an oligonucleotide comprising from 10 to 20 bases.

3. The method according to claim 1, wherein the target nucleic acid is mRNA.

4. The method according to claim 1, wherein the nuclear membrane unpermeable molecule is at least one member selected from the group consisting of proteins, sugars, beads, and metal particles.

5. The method according to claim 1, wherein the detection probe further contain a nuclease-blocking molecule that is bound thereto via a linker.

6. The method according to claim 5, wherein the nuclease-blocking molecule is identical with the nuclear membrane unpermeable molecule.

7. The method according to claim 1, wherein the detection probe comprises a first probe member and a second probe member, the first and second probe members have base sequences capable of hybridizing to the target nucleic acid adjacently with each other, the first probe member is labeled with an energy donor fluorescent dye and the second probe member is labeled with an energy acceptor fluorescent dye, the change in fluorescence of the fluorescent dyes is fluorescence resonance energy transfer (FRET) from the energy donor fluorescent dye of the first probe member to the energy acceptor fluorescent dye of the second probe member.

8. The method according to claim 7, wherein each of the first and the second probe members is an oligonucleotide comprising from 10 to 20 bases.

* * * * *